(12) United States Patent
Gelbin et al.

(10) Patent No.: US 8,183,311 B2
(45) Date of Patent: May 22, 2012

(54) LIQUID PHOSPHITE COMPOSITION DERIVED FROM CRESOLS

(75) Inventors: Michael E. Gelbin, Middlebury, CT (US); Maurice Power, Manchester (GB); Jonathan Hill, Manchester (GB)

(73) Assignee: Chemtura Corporation, Middlebury, CT (US)

( * ) Notice: Subject to any disclaimer, the term of this patent is extended or adjusted under 35 U.S.C. 154(b) by 96 days.

(21) Appl. No.: 12/534,035

(22) Filed: Jul. 31, 2009

(65) Prior Publication Data

US 2010/0076125 A1  Mar. 25, 2010

Related U.S. Application Data

(63) Continuation-in-part of application No. 11/787,531, filed on Apr. 16, 2007.

(60) Provisional application No. 60/815,819, filed on Jun. 20, 2006.

(51) Int. Cl.
  *C08K 5/51*  (2006.01)
  *C08K 5/34*  (2006.01)

(52) U.S. Cl. ......................... 524/128; 524/100

(58) Field of Classification Search .................. 524/128
  See application file for complete search history.

(56) References Cited

U.S. PATENT DOCUMENTS

| | | | |
|---|---|---|---|
| 2,220,845 A | 11/1940 | Moyle |
| 2,834,798 A | 5/1958 | Hechenbleikner et al. |
| 3,412,064 A | 11/1968 | Brindell |
| 3,492,377 A | 1/1970 | Kline |
| 3,558,554 A | 1/1971 | Kuriyama et al. |
| 3,644,536 A | 2/1972 | Bafford |
| 3,755,200 A | 8/1973 | Rhodes et al. |
| 3,756,906 A | 9/1973 | Nicholas et al. |
| 3,787,537 A | 1/1974 | De Marcq |
| 4,261,880 A | 4/1981 | Fujii et al. |
| 4,276,233 A | 6/1981 | Markezich et al. |
| 4,290,941 A | 9/1981 | Zinke et al. |
| 4,321,218 A | 3/1982 | Rasberger |
| 4,383,950 A | 5/1983 | Rasberger |
| 4,406,842 A | 9/1983 | Spivack |
| 4,492,661 A | 1/1985 | Maul et al. |
| 4,829,112 A | 5/1989 | Ishii et al. |
| 5,208,368 A | 5/1993 | Scherzer et al. |
| 5,254,610 A | 10/1993 | Small, Jr. et al. |
| 5,254,709 A | 10/1993 | Hunter |
| 5,322,871 A | 6/1994 | Pitteloud et al. |
| 5,401,845 A | 3/1995 | Pitteloud et al. |
| 5,532,401 A | 7/1996 | Stevenson et al. |
| 5,561,181 A | 10/1996 | Mahood |
| 6,576,788 B1 | 6/2003 | Penzel et al. |
| 6,824,711 B2 | 11/2004 | Stevenson et al. |
| 6,846,859 B2 | 1/2005 | Coffy et al. |
| 6,887,926 B1 | 5/2005 | Parhar et al. |
| 7,157,511 B2 | 1/2007 | Bobsein et al. |
| 7,176,252 B2 | 2/2007 | Stevenson et al. |
| 7,320,764 B2 | 1/2008 | Stevenson et al. |
| 7,361,703 B2 | 4/2008 | Tikuisis et al. |
| 7,468,410 B2 | 12/2008 | Chafin et al. |
| 2003/0078340 A1 | 4/2003 | Fatnes et al. |
| 2004/0048958 A1 | 3/2004 | Didier |
| 2007/0149660 A1 | 6/2007 | Kumar et al. |
| 2007/0228343 A1 | 10/2007 | Roth et al. |

FOREIGN PATENT DOCUMENTS

| | | |
|---|---|---|
| CZ | 8901540 | 1/1993 |
| DE | 2940620 | 4/1981 |
| EP | 0 090 524 | 10/1983 |
| EP | 0 245 852 | 11/1987 |
| EP | 0551 062 | 7/1993 |
| GB | 1 298 248 | 11/1972 |
| GB | 2039282 | * 1/1979 |
| GB | 2 227 490 | 8/1990 |
| JP | 59030842 | 2/1984 |
| JP | 5202236 | 8/1993 |
| JP | 7 309884 | 11/1995 |
| RO | RO112871 | 1/1998 |
| RU | 2 140 938 | 11/1999 |
| WO | 2007/149143 | 12/2007 |

OTHER PUBLICATIONS

International Preliminary Report on Patentability mailed Dec. 22, 2008; of PCT Application No. PCT/US2007/009690; 6 pgs.
Dover Chemical Company—Data Sheet "Doverphos Liquid Phosphites" (2011).

* cited by examiner

*Primary Examiner* — Ling Choi
*Assistant Examiner* — Hui Chin
(74) *Attorney, Agent, or Firm* — Joseph Suhadolnik

(57) ABSTRACT

A composition at least two different phosphites, one of which is derived from an alkylated cresol, wherein the composition is a liquid at ambient conditions. The other phosphites may be derived from alkylated cresol, alkylated phenol or other alkylated hydroxyaryl compounds. The cresol may be mono-alkylated or di-alkylated with a $C_1$-$C_{18}$ alkyl group.

10 Claims, No Drawings

LIQUID PHOSPHITE COMPOSITION DERIVED FROM CRESOLS

CROSS REFERENCE TO RELATED APPLICATIONS

This application is a continuation-in-part application of U.S. application Ser. No. 11/787,531, filed Apr. 16, 2007, which claims priority to U.S. Provisional Application No. 60/815,819, filed Jun. 20, 2006. Each of these applications is incorporated herein by reference in its entirety.

FIELD OF THE INVENTION

The present invention relates to a novel liquid phosphite composition suitable as antioxidants for polymers and methods for making the same. It also relates to stabilized polymers and stabilizer concentrates comprising a phosphite composition derived from one or more cresols.

BACKGROUND OF THE INVENTION

Organic phosphites are well-known and are commonly used as secondary antioxidants in polymer compositions including, for example, polyolefins, polyvinyl chloride, and elastomers. Examples of such phosphites are disclosed in H. Zweifel (Ed) *Plastics Additives Handbook,* 5th edition, Hanser Publishers, Munich 2000. Phosphite stabilizers, both liquid and solid, are known in the art.

Many of the most effective organic phosphites are solids at ambient temperature and accordingly do not lend themselves to being processed with certain polymers. Owing to their solid form and concomitant processing limitations, for example, some solid alkylaryl phosphites have been demonstrated to plateout during processing in some plastics, in particular low melting point plastics, and form deposits on processing machinery surfaces. In addition, solid organic phosphites typically must be processed, e.g., heated and melted, in order to be incorporated into the respective polymer compositions thereby increasing handling and processing costs.

One of the most widely used solid organic phosphites is tris(2,4-di-t-butylphenyl) phosphite, which is commercially sold under the trade name Alkanox™ 240 (Chemtura Corporation, Middlebury, Conn., USA), Irgafos™ 168 (Ciba Specialty Chemicals Corporation, Tarrytown, N.Y., USA), or Doverphos™ S-480 (Dover Chemical Corp, Dover, Ohio, USA). Tris(2,4-di-t-butylphenyl)phosphite has processability and solubility limitations, however, due to its solid form.

Liquid phosphite compositions are also well known and do not possess the handling problems associated with solid phosphite compounds. In addition, liquid phosphite compositions generally exhibit better processability than solid phosphite compositions for polymers that process at low temperatures. Tris(p-nonylphenyl)phosphite (TNPP), for example, is one alkylaryl phosphite that is a stable liquid at ambient conditions.

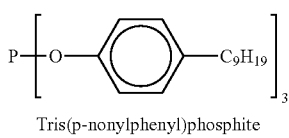

Tris(p-nonylphenyl)phosphite

TNPP is a versatile phosphite stabilizer that is useful in stabilizing a large number of polymers such as HDPE, LLDPE, SBR, ABS, PVC and others.

Most commercially available alkylaryl phosphites are derived from phenols. U.S. Pat. No. 5,254,709, for example, the entirety of which is incorporated herein by reference, describes the synthesis of tris(2,4-di-tert-butyl)phenyl phosphite by reacting an alkylated phenol intermediate, i.e., 2,4-di-tert-butyl phenol, with phosphorus trichloride in the presence of catalyst according to the following reaction:

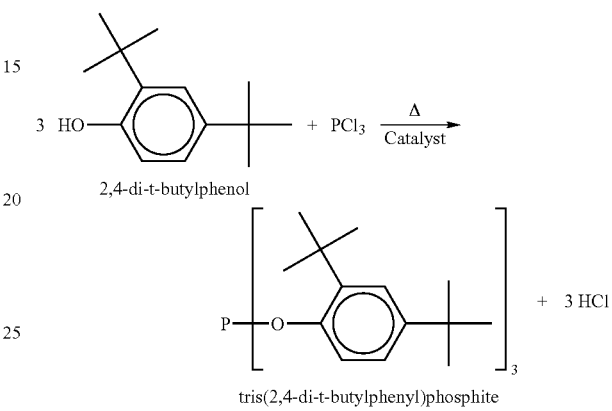

Generally, phosphites derived from phenols may include some residual phenols, which may present health and/or environmental issues. Para-nonylphenol, for example, which is used in synthesizing TNPP, has alleged estrogenic effects. Thus, the need exists for novel alkylaryl phosphites and for methods for making such alkylaryl phosphites. Several non-phenol sources have been proposed to make phosphites in the following patent literature.

GB Patent No. 2,227,490 describes reacting a 2-methyl-6-t-butyl-phenol, e.g., a 6-t-butyl-ortho-cresol, and biphenyl with a phosphorous trichloride to form a composition of: 0-5 mol % of 2-methyl-6-t-butyl-phenol; 35-45 mol % of tris(2-methyl-6-t-butyl-phenyl)phosphite; 10-20 mol % of bis(2-methyl-6-t-butyl-phenyl)biphenyl phosphonite; 30-40 mol % of bis(2-methyl-6-t-butyl-phenyl)biphenyl diphosphonite. The individual phosphites and phosphonites are separated and used as secondary antioxidants.

U.S. Pat. No. 3,558,554 describes various individual phosphites including di-n-butyl(2-t-butyl-p-cresyl)phosphite, di-n-hexyl(2-t-butyl-m-cresyl)phosphite, di-n-hexyl(2-t-butyl-p-cresyl)phosphite, di-n-octyl(2-t-butyl-p-cresyl)phosphite, di-n-butyl(2,6-di-t-butyl-p-cresyl)phosphite, di-phenyl(2-t-butyl-p-cresyl)phosphite, tri(2-t-butyl-p-cresyl) phosphite, di(ethylthioethyl)(2-t-butyl-p-cresyl)phosphite, and di(octylthioethyl)(2-t-butyl-p-cresyl)phosphite.

U.S. Pat. No. 4,261,880 describes tricresylphosphate.

U.S. Pat. No. 4,383,950 describes various individual phosphites including tris(di-2-t-octyl-4-methylphenyl)phosphite, tris(di-2-t-octyl-4-t-butyl-5-methylphenyl)phosphite, and tris(di-2-t-butyl-4-t-octyl-5-methylphenyl)phosphite.

U.S. Pat. No. 4,406,842 describes a O,O'-bis(2-t-octyl-4-methylphenyl)phenyl phosphite as a secondary stabilizer.

U.S. Pat. No. 5,322,871 describes bis(2,4-di-alkyl-o-cresyl)phosphite derivatives, including bis(2,4-di-t-butyl-6-methylphenyl)4-nonylphenyl phosphite and bis(2,4-di-t-butyl-6-methylphenyl)4-t-butyl-phenyl phosphite as secondary antioxidants.

U.S. Pat. No. 6,887,926 describes secondary stabilizers including: bis(2,6-di-t-butyl-4-methylphenyl)pentarythritol diphosphite, bis(2,4-di-t-butyl-6-methylphenyl)pentarythritol diphosphite, bis(2,4-di-t-butyl-6-methylphenyl)methyl phosphite and bis(2,4-di-t-butyl-6-methylphenyl)ethyl phosphite.

Notwithstanding the above literature, the need remains for safe and effective phosphite stabilizers for polymers against heat and light degradation and that are liquid at ambient conditions.

SUMMARY OF THE INVENTION

In a first aspect, the invention is directed to a composition comprising at least two different phosphites, wherein one of the at least two different phosphites is derived from an alkylated cresol, and wherein the composition is a liquid at ambient conditions. In one embodiment, the different phosphites are derived from a mixture of cresols, such as a mixture of alkylated m-cresol and alkylated p-cresol. In one embodiment, the different phosphites are derived from an alkylated cresol and an alkylated phenol.

In a second aspect, the invention is directed to a composition comprising a polymer and a secondary antioxidant composition comprising at least two different phosphites, wherein one of the at least two different phosphites is derived from an alkylated cresol, and wherein the secondary antioxidant composition is a liquid at ambient conditions. The composition may further comprises a primary antioxidant, such as a phenol antioxidant.

In a third aspect, the invention is directed to a method for forming a phosphite composition comprising at least two different phosphite compounds, the process comprising the step of reacting at least one alkylated cresol with a phosphorous halide under conditions effective to form the phosphite composition, and wherein the phosphite composition is a liquid at ambient conditions. In one embodiment, the alkylated cresol is selected from the group consisting of alkylated o-cresol, alkylated m-cresol, alkylated p-cresol, and mixtures thereof. Optionally, the reaction with the phosphorous halide may further comprise reacting at least one alkylated hydroxyaryl compound, e.g., an alkylated phenol, with the phosphorous halide.

DETAILED DESCRIPTION OF THE INVENTION

Introduction

The present invention relates to liquid phosphite compositions derived from one or more cresols, preferably from one or more alkylated cresols such as butylated cresols, amylated cresols or mixtures thereof, and to processes for forming such phosphite compositions. In one embodiment, there is a liquid phosphite composition derived from at least one cresol and at least one phenol. In one embodiment there is provided an alkylate composition derived from one or more cresols that are useful intermediates for forming such phosphite compositions and to processes for forming such alkylate compositions.

Alkylaryl phosphite compositions that comprise aryl moieties having tertiary alkyl groups, e.g., t-butyl or t-amyl, in the ortho position have proven highly effective as secondary antioxidants for polymer stabilization and generally possess good color quality. As a result, alkylated compositions that are ortho-substituted with tertiary alkyl groups are sought after as intermediates for forming such alkylaryl phosphite compositions. According to one embodiment of the invention, the alkylates are derived from m-cresol, p-cresol, or mixtures thereof to promote ortho substitution. In addition, the use of alkylated cresols in forming phosphite compositions increases complexity of the composition and in turn increases the liquidity of the phosphite composition, and improves solubility/compatibility with the polymer to be stabilized.

In addition to the ortho substitution, phosphite compounds with higher phosphorous content have more activity; the greater the phosphorous content, the greater the expected secondary antioxidant effect of the phosphite composition. According to another embodiment of the invention, the alkylate composition is derived from o- and/or p-cresol. Since the cresylic methyl groups block alkylation at one position, the overall phosphorus content and hence activity of the resulting alkylaryl phosphite composition may be increased relative to alkylaryl phosphites formed from comparable alkylate compositions derived from phenol.

Phosphite Compositions Derived from Cresols

In one embodiment, the present invention generally relates to a phosphite composition comprising at least two different phosphites of the structure

wherein $R_1$, $R_2$, and $R_3$ are independently selected alkylated aryl groups, provided that at least one alkylated aryl group is an alkylated cresyl group, and wherein the composition is a liquid at ambient conditions. By "ambient conditions" it is meant room temperature, e.g., 25° C., and 1 atmosphere pressure.

The aryl moiety present in the compounds of the present invention is preferably an aromatic moiety of from 6 to 18 carbon atoms, e.g., phenyl, naphthyl, phenanthryl, anthracyl, biphenyl, terphenyl, cresyl, xylenyl, and the like, preferably phenyl.

The cresyl moieties present in the compounds of the present invention are independently selected from the group consisting of o-cresyl, m-cresyl, p-cresyl, and mixtures thereof. The cresyl moiety, as well as any other aryl moiety, may be substituted with at least one alkyl group independently selected from straight-chain or branched $C_1$-$C_{18}$ alkyl, e.g., $C_1$-$C_8$ alkyl, $C_4$-$C_6$ alkyl or $C_4$-$C_5$ alkyl, $C_4$ alkyl or $C_5$ alkyl. The alkyl substituent may include, for example, methyl, ethyl, propyl, butyl, amyl, hexyl, heptyl, octyl, nonyl (although less preferred), decyl, undecyl, dodecyl, tridecyl, tetradecyl, pentadecyl, hexadecyl, heptadecyl, octadecyl, and isomers thereof. Preferably, the alkyl substituent(s) is not $C_8$-$C_{10}$ alkyl, e.g., not $C_9$ alkyl. As indicated, in a preferred embodiment, the alkyl moieties do not include nonyl, meaning the phosphite mixture preferably comprises less than 50 wppm, e.g., less than 10 wppm or less than 5 wppm nonyl substituted aryl phosphite compounds, and most preferably no detectable nonyl substituted aryl phosphite compounds. In addition, the phosphite composition preferably comprises less than 50 wppm, e.g., less than 10 wppm or less than 5 wppm nonylphenol, and most preferably no detectable nonylphenol. Most preferably, the alkyl group(s) are independently selected from propyl, butyl, especially, isopropyl, sec-butyl, tert-butyl, amyl, especially sec-amyl, tert-amyl neoamyl, and dodecyl. The cresyl moieties may be mono, di or tri substituted (not including the cresylic methyl group) in the ortho and/or para positions, but preferably the phosphites themselves are not exclusively trialkylated cresyl groups.

In a preferred embodiment, the phosphite composition comprises at least two different phosphites, e.g., at least three different phosphites, or at least four different phosphites, selected from the group consisting of a tris(dialkylcresyl) phosphite, tris(monoalkylcresyl)phosphite, bis(dialkylcresyl)monoalkylcresyl phosphite, bis(monoalkylcresyl)dialkylcresyl phosphite, tris(dialkylaryl)phosphite, tris(monoalkylaryl)phosphite, bis(dialkylaryl)monoalkylaryl phosphite, bis(monoalkylaryl)dialkylaryl phosphite, bis(dialkylaryl)monoalkylcresyl phosphite, bis(monoalkylcresyl)dialkylaryl phosphite, bis(dialkylcresyl)monoalkylaryl phosphite, and bis(monoalkylaryl)dialkylcresyl phosphite, provided that at least one phosphite has a cresyl moiety. The aryl moiety preferably is phenyl.

In one embodiment, the phosphite composition comprises at least one phosphite selected from the group consisting of tris(dialkylaryl)phosphite, tris(monoalkylaryl)phosphite, tris(monoalkylcresyl)phosphite, bis(dialkylcresyl)monoalkylcresyl phosphite, bis(monoalkylcresyl)dialkylcresyl phosphite, bis(dialkylaryl)monoalkylcresyl phosphite, bis(monoalkylcresyl)dialkylaryl phosphite, bis(dialkylcresyl)monoalkylaryl phosphite, and bis(monoalkylaryl)dialkylcresyl phosphite, provided that at least one phosphite has a cresyl moiety.

In one embodiment, the phosphite composition includes at least one phosphite compound having a mono-substituted cresyl moiety, e.g., a tris(monoalkylcresyl)phosphite, bis(dialkylcresyl)monoalkylcresyl phosphite, bis(monoalkylcresyl)dialkylcresyl phosphite, bis(dialkylaryl)monoalkylcresyl phosphite, bis(monoalkylcresyl)dialkylaryl phosphite, bis(dialkylcresyl)monoalkylaryl phosphite, and bis(monoalkylaryl)dialkylcresyl phosphite. Preferably the mono-substituted cresyl moiety is a m-cresyl, p-cresyl, or a mixture thereof.

In one embodiment, $R_1$, $R_2$, and $R_3$ are independently selected alkylated cresyl groups of the structure:

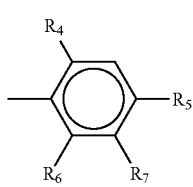

(III)

wherein $R_4$, $R_5$, and $R_6$ are independently selected from the group consisting of hydrogen and $C_1$-$C_8$ alkyl, e.g., methyl, ethyl, propyl, butyl, amyl, hexyl, heptyl, octyl, and isomers thereof, e.g., isopropyl, tert-butyl, tert-amyl, neo-amyl, and $R_7$ is hydrogen or methyl, provided that at least one of $R_1$, $R_2$, and $R_3$ comprises a moiety of structure (III) wherein at least one of $R_4$, $R_5$, $R_6$, and $R_7$ is methyl and at least two of $R_4$, $R_5$, $R_6$, and $R_7$ are $C_1$-$C_8$ alkyl. In one embodiment, each of $R_1$, $R_2$, and $R_3$ comprises a moiety wherein at least one of $R_4$, $R_5$, $R_6$, and $R_7$ is methyl and another of one of $R_4$, $R_5$, $R_6$, and $R_7$ is $C_1$-$C_8$ alkyl. Preferably, for each of $R_1$, $R_2$, and $R_3$, at least one (optionally two or three) of $R_4$, $R_5$, and $R_6$ comprises an alkyl group having a tertiary α-carbon, e.g., t-butyl or t-amyl, and at least one of $R_4$, $R_5$, $R_6$, and $R_7$ comprises a methyl group. Most preferably, the alkyl group(s) for $R_4$, $R_5$, and $R_6$ are independently selected from hydrogen, propyl, butyl, especially, isopropyl, sec-butyl and tert-butyl, amyl, especially sec-amyl, tert-amyl and neo-amyl, and dodecyl.

In various optional embodiments, at least one phosphite derived from cresol has at least one $R_1$, $R_2$, and $R_3$ that is independently selected from the groups listed in Table 1. Of course, it is contemplated that one or more of $R_1$, $R_2$, and $R_3$ may comprise an alkylated phenol or an unalkylated cresol provided that at least one of $R_1$, $R_2$, and $R_3$ are independently selected from the groups listed in Table 1.

TABLE 1

| | $R_1$, $R_2$ or $R_3$ | | |
|---|---|---|---|
| $R_4$ | $R_5$ | $R_6$ | $R_7$ |
| Me | H | t-butyl or t-amyl | H |
| Me | t-butyl or t-amyl | H | H |
| Me | t-butyl or t-amyl | t-butyl or t-amyl | H |
| H | Me | t-butyl or t-amyl | H |
| t-butyl or t-amyl | Me | H | H |
| t-butyl or t-amyl | Me | t-butyl or t-amyl | H |
| H | t-butyl or t-amyl | Me | H |
| t-butyl or t-amyl | H | Me | H |
| t-butyl or t-amyl | t-butyl or t-amyl | Me | H |
| t-butyl or t-amyl | H | H | Me |
| H | t-butyl or t-amyl | H | Me |
| H | H | t-butyl or t-amyl | Me |
| t-butyl or t-amyl | t-butyl or t-amyl | H | Me |
| t-butyl or t-amyl | H | t-butyl or t-amyl | Me |
| H | t-butyl or t-amyl | t-butyl or t-amyl | Me |
| t-butyl or t-amyl | t-butyl or t-amyl | t-butyl or t-amyl | Me |

In one embodiment of the present invention, the phosphite composition comprises at least two different phosphites, wherein one of the phosphites is derived from an alkylated m-cresol selected from the group consisting of tris(4-t-butyl-m-cresyl)phosphite, tris(2-t-butyl-m-cresyl)phosphite, tris(4,6-di-t-butyl-m-cresyl)phosphite, bis(4-t-butyl-m-cresyl)-4,6-di-t-butyl-m-cresyl phosphite, bis(2-t-butyl-m-cresyl)-4-t-butyl-m-cresyl phosphite, bis(2-t-butyl-m-cresyl)-4,6-di-t-butyl-m-cresyl phosphite, bis(4,6-di-t-butyl-m-cresyl)-4-t-butyl-m-cresyl phosphite, bis(4,6-di-t-butyl-m-cresyl)-2-t-butyl-m-cresyl phosphite, tris(4-t-amyl-m-cresyl)phosphite, tris(2-t-amyl-m-cresyl)phosphite, tris(4,6-di-t-amyl-m-cresyl)phosphite, bis(4-t-amyl-m-cresyl)-2-t-amyl-m-cresyl phosphite, bis(4-t-amyl-m-cresyl)-4,6-di-t-amyl-m-cresyl phosphite, bis(2-t-amyl-m-cresyl)-4-t-amyl-m-cresyl phosphite, bis(2-t-amyl-m-cresyl)-4,6-di-t-amyl-m-cresyl phosphite, bis(4,6-di-t-amyl-m-cresyl)-4-t-amyl-m-cresyl phosphite, and bis(4,6-di-t-amyl-m-cresyl)-2-t-amyl-m-cresyl phosphite. It is noted that tris(4,6-di-t-butyl-m-cresyl)phosphite may also be referred to as tris(2,4-di-t-butyl-3-methylphenyl)phosphite.

In yet another preferred embodiment of the present invention, the phosphite composition comprises at least two different phosphites, wherein one of the phosphites is derived from alkylated p-cresol selected from the group consisting of tris(2-t-butyl-p-cresyl)phosphite, tris(2,6-di-t-butyl-p-cresyl)phosphite, bis(2-t-butyl-p-cresyl)-2,6-di-t-butyl-p-cresyl phosphite, bis(2,6-di-t-butyl-p-cresyl)-2-t-butyl-p-cresyl phosphite, tris(2-t-amyl-p-cresyl)phosphite, tris(2,6-di-t-amyl-p-cresyl)phosphite, bis(2-t-amyl-p-cresyl)-2,6-di-t-amyl-p-cresyl phosphite, and bis(2,6-di-t-amyl-p-cresyl)-2-t-amyl-p-cresyl phosphite. Preferably, the phosphite composition comprises at least one of the m-cresyl phosphites as identified above and at least one of the p-cresyl phosphites as identified above.

As shown above, the phosphite compositions as described as prepared from one isomer of cresol. In still further embodiments the phosphite composition may be prepared from a mixture of cresol isomers, e.g., o-cresol and m-cresol, o-cresol and p-cresol, m-cresol and p-cresol, and o-cresol, m-cresol and p-cresol. A mixture of m-cresol and p-cresol is preferred. It should be understood that the phosphite composition would comprise a mixture of any of the phosphites identified above. Generally the molar ratio of cresol isomers would be from 1:9 to 9:1, e.g., from 1:4 to 4:1, or from 2:3 to 3:2. In one embodiment, there is a combination of alkylated m-cresol present in an amount from 5-95 wt. %, e.g., 30-70 wt. % or 40-60 wt. %, and alkylated p-cresol present in an amount from 5-95 wt. %, e.g., 30-70 wt. % or 40-60 wt. %. In one preferred embodiment there is a mixture of 30-70 wt. % alkylated m-cresol and 30-70 wt % of alkylated p-cresol. The m-cresol or p-cresol may be both be mono-substituted, e.g., 4-t-butyl-m-cresol, 6-t-butyl-m-cresol, and 2-t-butyl-p-cresol.

In further embodiments, the phosphite composition may be derived from a combination of alkylated cresols and alkylated phenols. Preferred combinations include: an alkylated p-cresol and an alkylated phenol, an alkylated m-cresol and an alkylated phenol, or a mixture of alkylated m-cresol/p-cresol and an alkylated phenol combinations. The alkyl group on the alkylated cresols may be the same or different alkyl group that is on the alkylated phenols, and preferably is selected from t-butyl and t-amyl. The ratio of alkylated cresols to alkylated phenols may be from 1:9 to 9:1, e.g., from 1:4 to 4:1, or from 2:3 to 3:2. In one embodiment, there is a combination of alkylated cresol present in an amount from 5-95 wt. %, e.g., 30-70 wt. % or 40-60 wt. %, and alkylated phenol present in an amount from 5-95 wt. %, e.g., 30-70 wt. % or 40-60 wt. %. In one embodiment there is a mixture of 30-70 wt. % alkylated m-cresol and 30-70 wt % of alkylated phenol. In another embodiment there is a composition of 30-70 wt. % alkylated p-cresol and 30-70 wt % of alkylated phenol. In another embodiment there is a composition of 30-70 wt. % phosphites derived from cresols and 30-70 wt. % of phosphites derived from phenols.

As indicated above, in a preferred embodiment, the phosphite composition comprises at least two phosphites, provided that at least one phosphite is derived from cresol, and wherein the phosphite composition is a liquid at ambient conditions. The relative amounts of the respective phosphite components contained in these phosphite compositions may vary somewhat within the inventive ranges so long as the phosphite composition itself is a liquid at ambient conditions. In terms of ranges, for example, the phosphite composition preferably comprises a tris(monoalkylaryl)phosphite, e.g., tris(4-t-amyl-phenyl)phosphite and/or tris(4-t-amyl-m-cresyl)phosphite, in an amount from 20 to 70 wt. %, e.g., from 15 to 55 wt. %, or from 37 to 54 wt. % and a bis(monoalkylaryl)dialkylaryl phosphite, e.g., bis(4-t-amyl-phenyl)-4,6-di-t-amyl-m-cresyl)phosphite, bis(4-t-amyl-phenyl)-4,6-di-t-amyl-m-cresyl)phosphite and/or bis(4-tert-amyl-m-cresyl)-4,6-di-tert-amyl-m-cresyl)phosphite, in an amount from 15 to 60 wt. %, e.g., from 31 to 50 wt. % or from 34 to 45 wt. %. Optionally, the phosphite composition further comprises a tris(dialkylaryl)phosphite, and/or bis(dialkylaryl) monoalkylaryl phosphite. If present, the tris(dialkylaryl) phosphite, e.g., tris(2,4-di-tert-amyl-phenyl)phosphite, and/or tris(4,6-di-tert-amyl-m-cresyl)phosphite, preferably is present in an amount of from 0.1 to 20 wt. %, e.g., from 0.3 to 5 wt. %, or from 0.5 to 1 wt. %. If present, the bis(dialkylaryl) monoalkylaryl phosphite, e.g., bis(2,4-di-tert-amyl-phenyl)-4-t-amyl-phenyl phosphite, bis(4,6-di-tert-amyl-m-cresyl)-4-t-amyl-m-cresyl phosphite, bis(2,4-di-tert-amyl-phenyl)-4-t-amyl-m-cresyl phosphite, and/or bis(4,6-di-tert-amyl-m-cresyl)-4-t-amyl-phenyl phosphite, preferably is present in an amount of from 2 to 20 wt. %, e.g., from 4 to 20 wt. %, or from 5 to 10 wt. %. In these embodiments, at least one of the phosphites has an alkylated cresyl moiety. Unless otherwise indicated, weight percent (wt. %) is based on the total weight of all phosphite components in the phosphite composition.

In a preferred embodiment, the phosphite composition comprises at least two of tris(di-$C_3$-$C_5$ alkylcresyl)phosphite, tris(di-$C_3$-$C_5$ alkylphenyl)phosphite, tris($C_3$-$C_5$ alkylcresyl) phosphite, tris($C_3$-$C_5$ alkylphenyl)phosphite, a bis(di-$C_3$-$C_5$ alkylcresyl)$C_3$-$C_5$ alkylcresyl phosphite, a bis(di-$C_3$-$C_5$ alkylcresyl)$C_3$-$C_5$ alkylphenyl phosphite, a bis(di-$C_3$-$C_5$ alkylcresyl)$C_3$-$C_5$ alkylphenyl phosphite, a bis(di-$C_3$-$C_5$ alkylphenyl)$C_3$-$C_5$ alkylphenyl phosphite, a bis($C_3$-$C_5$ alkylphenyl) di-$C_3$-$C_5$ alkylcresyl phosphite, and a bis($C_3$-$C_5$ alkylcresyl) di-$C_3$-$C_5$ alkylcresyl phosphite. Preferably, the composition comprises each of the following phosphites in the following amounts: 0.5 to 1 wt. % of a tris(di-$C_3$-$C_5$ alkylcresyl)phosphite or tris(di-$C_3$-$C_5$ alkylphenyl)phosphite; 37 to 54 wt. % of a tris($C_3$-$C_5$ alkylcresyl)phosphite or tris($C_3$-$C_5$ alkylphenyl)phosphite; 5 to 10 wt. % of a bis(di-$C_3$-$C_5$ alkylcresyl) $C_3$-$C_5$ alkylcresyl phosphite, bis(di-$C_3$-$C_5$ alkylcresyl)$C_3$-$C_5$ alkylphenyl phosphite, bis(di-$C_3$-$C_5$ alkylphenyl)$C_3$-$C_5$ alkylcresyl phosphite, or bis(di-$C_3$-$C_5$ alkylphenyl)$C_3$-$C_5$ alkylphenyl phosphite; and 34 to 40 wt. % of a bis($C_3$-$C_5$ alkylcresyl)di-$C_3$-$C_5$ alkylcresyl phosphite, bis($C_3$-$C_5$ alkylcresyl) di-$C_3$-$C_5$ alkylphenyl phosphite, bis($C_3$-$C_5$ alkylphenyl)di-$C_3$-$C_5$ alkylcresyl phosphite, or bis($C_3$-$C_5$ alkylphenyl)di-$C_3$-$C_5$ alkylphenyl phosphite.

As suggested above, the phosphite composition of the invention may be characterized based on how the cresyl moieties are substituted as a whole. In this context, "substituted" is meant to refer to any alkyl substituent groups, e.g., t-amyl or t-butyl groups, other than the methyl group associated with the cresyl group. For example, in one embodiment where the phosphites are derived from m-cresol and p-cresol mixture, a majority of the m-cresyl moieties are para-substituted, e.g., at least 80 wt. % para-substituted, at least 85 wt. % para-substituted, or at least 90 wt. % para-substituted.

As indicated above, the phosphite composition of the invention includes a composition of phosphite compounds having cresyl moieties that are monoalkylated and dialkylated. Ideally, few if any of the cresyl moieties are trisubstituted. For example, in some embodiments fewer than 3 wt. % of the cresyl moieties are trisubstituted, e.g., fewer than 2 wt. %, or fewer than 1 wt. %. Preferably, the phosphite is not derived from 2,6-di-t-butyl-p-cresol, i.e., BHT.

Similarly, it is preferred that few if any of the o-cresyl moieties are mono-substituted in the ortho position. Note that mono-substituted for o-cresyl refers to alkylated at the ortho position opposite the ortho methyl group. Preferably, the cresyl moieties are mono-substituted in the ortho position in an amount less than 3 wt. %, e.g., less than 2 wt. % or less than 1 wt. %.

Preferably, the phosphite composition has a low level or is substantially free of cresols and/or other hydroxyaryls (phenols), whether alkylated or unalkylated, when contained in the phosphite composition. In terms of amounts, the phosphite composition preferably comprises less than 5 wt. %, e.g., less than 3 wt. % or less than 1 wt. %, of free cresols and/or phenols, based on the total weight of the phosphite composition. Any free phenolics, for example, may be removed by distillation. Extremely low levels of free cresols and/or phenols may be achieved, for example, by employing a wiped-film molecular (Short-Path) still, wiped film evaporator (WFE), thin film evaporator, or similar equipment. In terms of amounts, the phosphite composition may comprise less than 0.5 wt. %, e.g., less than 0.2 wt. % or less than 0.1 wt. %, of free cresols and/or phenols, based on the total weight of the phosphite composition.

In other embodiments, a minor amount of free cresols and/or phenols may be beneficial, for example, as a viscosity reducing agent. Thus, in one embodiment, the phosphite composition comprises a minor amount of free cresols and/or phenols, e.g., from 1 to 4 wt. %, e.g., from 2 to 3 wt. %, based on the total weight of the phosphite composition.

In addition, the phosphite compositions preferably are substantially free of phosphite compounds having unsubstituted cresyl or phenyl moieties, e.g., triphenylphosphites, tricresylphosphites, bis(cresyl)alkylcresyl phosphites or bis(alkylphenyl)cresyl phosphites. In terms of amounts, the phosphite composition preferably comprises less than 2 wt. %, e.g., less than 1 wt. % or less than 0.5 wt. %, phosphite compounds having at least one unsubstituted cresyl/phenyl moiety, based on the total weight of the phosphite composition.

In some preferred embodiments, the phosphite composition includes one or more hydrolytic stabilizers. Preferred stabilizers include amines of the structure:

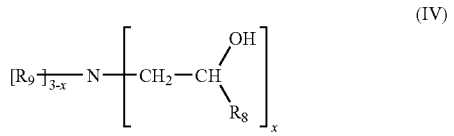

(IV)

wherein x is 1, 2 or 3; $R_8$ is selected from the group consisting of hydrogen, and straight or branched $C_1$-$C_6$ alkyl, and $R_9$ is selected from the group consisting of straight or branched $C_1$-$C_{30}$ alkyl. Preferably $R_8$ is selected from the group consisting of straight or branched $C_1$-$C_4$ alkyl, e.g., methyl or ethyl. Preferably $R_9$ is selected from the group consisting of straight or branched $C_5$-$C_{20}$ alkyl, e.g., straight or branched $C_{10}$-$C_{20}$ alkyl or straight or branched $C_{12}$-$C_{18}$ alkyl. In one embodiment, x is 1 and $R_9$ is straight or branched $C_5$-$C_{20}$ alkyl, e.g., $C_{12}$-$C_{18}$ alkyl. In one embodiment, x is 2 and $R_9$ is straight or branched $C_{10}$-$C_{20}$ alkyl, e.g., $C_{12}$-$C_{18}$ alkyl.

In one aspect the amine is selected from the group consisting of the triethanolamine, triisopropanolamine, diethanolamine, diisopropanolamine, and tetraisopropanolethylenediamine.

In another aspect the amine is selected from the group consisting of octyl-bis(2-ethanol)amine, nonyl-bis(2-ethanol)amine, decyl-bis(2-ethanol)amine, undecyl-bis(2-ethanol)amine, dodecyl-bis(2-ethanol)amine, tridecyl-bis(2-ethanol)amine, tetradecyl-bis(2-ethanol)amine, pentadecyl-bis(2-ethanol)amine, hexadecyl-bis(2-ethanol)amine, heptadecyl-bis(2-ethanol)amine, octadecyl-bis(2-ethanol)amine, octyl-bis(2-propanol)amine, nonyl-bis(2-propanol)amine, decyl-bis(2-propanol)amine, undecyl-bis(2-propanol)amine, dodecyl-bis(2-propanol)amine, tridecyl-bis(2-propanol)amine, tetradecyl-bis(2-propanol)amine, pentadecyl-bis(2-propanol)amine, hexadecyl-bis(2-propanol)amine, heptadecyl-bis(2-propanol)amine, octadecyl-bis(2-propanol)amine, and isomers thereof. Commercially available amines include Armostat™ 300 and Armostat 1800 manufactured by Akzo Nobel Polymers.

Additional hydrolytic stabilizers include epoxies such as epoxidized soybean oil (ESBO) commercially available as Drapex™ 39, Drapex 392, Drapex 4.4, and Drapex 6.8 (Chemtura Corp.).

The amine may be present in an amount of from 0.01 to 5 wt. %, e.g., from 0.1 to 1.5 wt. % or from 0.2 to 0.8 wt. %, based on the total weight of the phosphite composition.

As indicated above, the phosphite composition is a liquid at ambient conditions. As used herein, by "liquid," it is meant that the phosphite composition remains liquid after at least three "freeze/thaw" cycles as opposed to "meta-stable liquids," which do not remain liquids after three or fewer cycles. A freeze/thaw cycle is defined as follows: 1) An ambient temperature composition is stirred for 0.5 hours; 2) The stirred composition is then refrigerated at about 5° C. for three days; and 3) The refrigerated composition is then brought to ambient temperature and held at ambient for 3 days. Upon completion of step 3, the composition is checked for solids content, e.g., crystallization. Completion of steps 1-3 defines one freeze/thaw cycle.

As noted above, it is a feature of the present invention that the phosphite composition is in liquid physical form at ambient conditions. This is clearly surprising, given that the prior art teaches several examples of solid phosphite compositions, the components of which are separately solids at ambient condition, (See JP 59030842; WO 9303092; CA 2,464,551). In the present invention, in contrast, the phosphite composition is liquid even though the individual components are solid. For example, tris(2-t-butyl-p-cresyl)phosphite has a melting point of 111° C.

The viscosity of the phosphite composition may vary depending on the relative amounts of the various phosphite compounds contained therein. In some exemplary embodiments, the phosphite composition has a viscosity less than 11,000 cSt, e.g., less than 7,300 cSt, less than 5,000 cSt, less than 3,000 cSt, or less than 2850 cSt, these viscosities being measured at 30° C. In terms of ranges, viscosity of the composition may range from 1 cSt to 15,000 cSt, from 100 cSt to 12,000 cSt, from 500 cSt to 10,000 cSt, from 500 cSt to 6,500 cSt, from 500 cSt to 5,000 cSt, from 500 cSt to 3,000 cSt, from 1,000 cSt to 4,000 cSt, from 1,500 cSt to 3,500 cSt, from 2,000 cSt to 3,000 cSt, or from 2,000 to 2,800 cSt, these viscosities being measured at 30° C.

The present invention also relates to methods for making the above-described liquid phosphite compositions. In one embodiment, the liquid phosphite compositions may be made in the direct reaction of a phosphorus trihalide, e.g., phosphorus trichloride, and at least one, e.g., at least two, alkylated cresol and optionally one or more alkylated phenols. In various embodiments the cresols may be monoalkylated, dialkylated or trialkylated, e.g., with one or more tertiary alkyl groups such as t-butyl or t-amyl. If the cresol is ortho-cresol and/or para-cresol, the cresol preferably is monoalkylated or dialkylated. If the cresol is meta-cresol, the cresol may be monoalkylated, dialkylated or trialkylated. The liquid phosphite composition may be incorporated into a polymer as a secondary antioxidant.

In one embodiment, the phosphite compositions are derived from alkylated o-cresols and/or alkylated p-cresols, which may increase the phosphorous content of the liquid phosphite composition relative to phosphite compositions derived from alkylated phenols. The hydroxyl group of cresol compounds act as ortho or para directors, and the methyl group blocks one of the available positions on the aromatic ring. By blocking either of the ortho positions or the para position with the methyl group, the overall phosphorous content of the resulting phosphite may be advantageously increased over those formed from alkylated phenols that lack a blocking methyl group since one less ortho/para position is available for being alkylated with a tertiary alkyl group, e.g., t-butyl or t-amyl. In one embodiment, the phosphite composition has an overall phosphorus content that is equal to or greater than TNPP, e.g., at least 4.5 mole %, e.g., at least 4.8 mole %, or at least 5.1 mole %. In terms of ranges, the overall phosphorus content of the phosphite composition may range, for example, from 4.5 to 10.0 mole %, e.g., from 5.5 to 7.5 mole %, or 5.7 to 6.5 mole %, based on the total moles of all phosphorous-containing compounds in the phosphite composition.

P-cresols, and m-cresols to a lesser extent, promote alkylation at the ortho position. Directing to alkylation to the ortho position may be desired for alkylation with tertiary alkyl groups, e.g., t-butyl or t-amyl, as indicated above. In one embodiment, the phosphite composition is substantially free of phosphite compounds having m-cresyl or p-cresyl groups that are substituted with non-tertiary alkyl groups, meaning alkyl groups having hydrogen atoms at the α position. That is, in preferred embodiments, at least 95%, at least 98% or at least 99% of the cresyl moieties are substituted with alkyl groups having tertiary α-carbons, most preferably tert-butyl and/or tert-amyl.

Processes

Thus, the present invention also relates to processes for making alkylated compositions comprising two or more alkylated cresol compounds and to the alkylated compositions formed by such processes. The composition of the alkylated cresol compounds may be modified by varying types and ratios of the reactants and/or by modifying processing conditions.

The alkylated composition may be formed by contacting one or more cresol compounds with one or more olefins (e.g., isoamylene or isobutene) optionally in the presence of a catalyst and under conditions effective to form the alkylated composition. The one or more olefins preferably contain from 2 to 18 carbons, e.g., from 2 to 8 carbons, or from 4 to 6 carbons. As an alternative to using an olefin alkylating agent, one or more alkyl halides, alcohols, MTBE or TAME may be employed. The alkylating agent that is employed may comprise or be derived from a hydrocarbon stream comprising alkanes and alkenes, such as a petrochemical raffinate stream from a $C_4$ or $C_5$ fraction, or a dehydrogenation reaction product of an alkane. In this aspect, the alkanes pass through the alkylating process unaltered and may be easily separated from the product alkylated composition.

The ratio of olefin(s) to cresol(s)/phenol(s) preferably is such that the resulting alkylated composition is suitable for conversion to the desired phosphite composition when reacted with a phosphorous halide such that the resulting phosphite composition is a liquid at ambient conditions. In some exemplary embodiments, the molar ratio of olefin to hydroxyaryls, including cresol(s) and optionally phenol(s), ranges from 6:1 to 1:1, e.g., from 2:1 to 1.1:1 or from 1.4:1 to 1.25:1, although these ratios may very somewhat depending, for example, on the catalyst employed in the alkylation process and the desired composition and viscosity for the ultimately formed phosphite composition.

Although conditions for the alkylation process may vary widely, in some preferred embodiments, the reaction of the cresol, and optionally phenol, and the olefin may occur in an inert atmosphere (e.g., under nitrogen) at a temperature of from 60 to 160° C., e.g., from 70 to 145° C. or from 80 to 140° C. The reaction is preferably performed at a pressure of from 0.2 to 10 atm, e.g., from 0.2 to 5 atm or from 0.2 to 4 atm. In a batch reaction, the reaction time may last from 1 to 12 hours, e.g., from 2 to 10 hours, or from 3 to 5 hours. In a continuous reaction, the residence time may be from 0.1 to 5 hours, e.g., from 0.2 to 4 hours or from 0.5 to 1 hour. The alkylation preferably is performed in the presence of a catalyst. The catalyst may, for example, be selected from the group consisting of acid clay catalyst, cationic ion exchange resins, Brönsted acids, e.g., sulfuric acid, trifluoromethanesulfonic acid (triflic acid) and phosphotungstic acid, or Lewis acids, e.g., $BF_3$. Suitable commercial acid clay catalysts include Fulcat™ 22B (Rockwood Additives). In one embodiment, the sulfonic acid-type cation-exchange resin catalyst useful in the present invention can be, for example, a sulfonated styrene-divinyl benzene copolymer, a sulfonated crosslinked styrene polymer, a phenol formaldehyde-sulfonic acid resin, or a benzene formaldehyde-sulfonic acid resin. Cation exchange resins useful in the present invention include for example styrene-divinylbenzene types of strong acid ion exchange resins such as Dowex™ 50WX4, Dowex 50WX2, Dowex M-31, Dowex Monosphere M-31, Dowex DR-2030 and Dowex Monosphere DR-2030 catalysts (Dow Chemical). Other appropriate resins include: Amberlyst™ 15, Amberlyst 131, Amberlyst 35, Amberlyst 36, and A21 (Rohm and Hass, subsidiary of Dow); Diaion™ WA30, Diaion SK104, Diaion SK1B, Diaion PK208, Diaion PK212 and Diaion PK216 (Mitsubishi); Tulsion™ T-38, Tulsion T-62, Tulsion T-66, Tulsion T-3825 and Tulsion T-3830 (Thermax); Lewatit™ K1131, Lewatit K1221, Lewatit K1261 and Lewatit SC 104 (Sybron Chemicals); Indion™ 180 and Indion 225 (Ion Exchange (India) Limited); and Purolite™ CT-175, Purolite™ CT-169, and Purolite™ CT-275 (Purolite).

In one embodiment, a batch alkylate synthesis takes place in a pot-type reactor. In another embodiment, the alkylate synthesis is conducted on a continuous basis in a continuous type reactor. In the continuous process, the alkylation reaction is optionally quenched using a polar solvent, water, that forms a liquid phase containing most, if not all, of the catalyst and a organic phase containing the alkylated aryl compound, which may be removed by distillation. When the continuous process takes place over a fixed bed of solid catalyst a quenching step may not be necessary.

In one aspect of the process, any free cresol or phenol that is not reacted with the olefin may be removed from the mixture of reaction products through distillation at a temperature, for example, of from 70 to 160° C. and at a pressure of from 1 to 10 mbar.

In some embodiments, a mixed olefin and/or mixed cresol feedstock may be used to form a more diverse alkylated composition, which may be desired to ultimately form a more diverse phosphite composition. Thus, a mixture of lower alkenes (e.g., two or more $C_3$-$C_6$ olefins, such as a mixture of butylene and amylenes) may be reacted with the alkylated cresol either in parallel (feed in olefin A and B at the same time) or consecutively (i.e. olefin A is reacted first followed by olefin B).

As indicated above, depending on the desired composition (e.g., butylated and/or amylated) and target viscosity for the alkylated composition as well as the ultimately formed phosphite composition, the composition of the alkylated composition may vary widely. The alkylated composition may comprise, for example, from 5 to 95 wt. %, e.g., from 10 to 70 wt. % or from 30 to 65 wt. %, of a p-alkylated hydroxyaryl compound, and from 5 to 95 wt. %, e.g., from 10 to 70 wt. % or from 30 to 65 wt. %, of a o,p-dialkylated hydroxyaryl compound. In one embodiment, the p-alkylated hydroxyaryl compound is a p-t-butyl-m-cresol and the o,p-dialkylated hydroxyaryl compound is a 2,4-di-t-butyl-phenol.

In one embodiment, the alkylated composition, optionally formed from the above-described alkylated composition synthesis process, is further reacted with a phosphorus trihalide, with or without catalyst, to form a liquid phosphite composition. In one embodiment, the alkylated composition is selected from the group consisting of alkylated o-cresol, alkylated m-cresol, alkylated p-cresol, and mixtures thereof, and optionally includes at least one alkylated hydroxyaryl, such as alkylated phenols. The phosphorus trihalide preferably is selected from phosphorus trichloride and phosphorus tribromide. When a catalyst is used, the catalyst may be selected from the group consisting of pyridine, N,N-dimethyldodecylamine, dilauryl methyl amine, trialkylamine, and the hydrochloride salts thereof. The molar ratio of alkylated composition (i.e., alkylated cresol compounds) to phosphorus trihalide preferably is from 5:1 to 3:1, e.g., from 4:1 to 3:1 or from 3.7:1 to 3.1:1.

The reaction of the alkylated cresols and optionally alkylated phenols with a phosphorus trihalide may be conducted under an inert atmosphere (e.g., nitrogen) at a temperature of from 5 to 80° C., e.g., from 40 to 70° C. or from 50 to 70° C. The phosphorus trihalide may be charged to the reactor and the alkylate composition may be added thereto. In this case, preferably, the temperature is held at or below 70° C. during the addition of the phosphorus trihalide to the alkylate composition to prevent refluxing the phosphorus trihalide. After the addition of phosphorus trihalide, the temperature is optionally held for 10 minutes to 12 hours, e.g., from 30 minutes to 10 hours, or from 1 hour to 3 hours. The reaction preferably is conducted at a pressure of 0.8 to 4 atm, e.g., from 0.9 to 3 atm or from 1 to 2 atm. Optionally, the alkylate composition may be charged to the reactor and the phosphorus trihalide added thereto. Next the temperature may be ramped to 70° C. to 200° C., e.g., from 80° C. to 150° C. or from 90° C. to 120° C. Preferably, the reaction at the ramped temperature is for 10 minutes to 12 hours, e.g., from 30 minutes to 10 hours, or from 1 hour to 3 hours. The reaction preferably is conducted at a reduced pressure of 0.01 to 0.5 atm, e.g. from 0.03 to 0.4 atm or from 0.04 to 0.1 atm. During the reaction time, hydrochloric or hydrobromic gas will be evolved, and may be removed by reducing the pressure to about 0.05 atm or sweeping an inert gas such as nitrogen over the reaction mixture. In one aspect the removal of such gases may be performed until the total chloride content in the reaction mixture is less than 50 ppm, e.g., less than 25 ppm or less than 10 ppm.

In one aspect of the process, any free cresol or phenol that is not reacted with the phosphorus trihalide may be liberated by raising the reaction temperature to up to 275° C., e.g., up to 250° C. or up to 225° C., and in a vacuum at a pressure of 0.0001 to 0.1 atm. In one embodiment, a wiped-film molecular (Short-Path) stills, wiped film evaporators (WFE), thin film evaporators, or similar equipment may be used to further remove the free cresol or phenol.

In one embodiment, the step of forming the phosphite composition may occur in one or more neutral solvents. Typical solvents that may be employed include toluene, xylene, methylene chloride, heptane, chloroform, and benzene.

In one embodiment, the liquid phosphite composition of the present invention are obtained in a direct chemical reaction, in which the molar ratio of the alkylated cresol is adjusted to yield a phosphite composition that is a liquid at ambient conditions. A schematic of one exemplary reaction method is shown below. In this embodiment, an alkylated composition comprising a monoalkyl-m-cresol and a dialkyl-m-cresol is reacted with PCl₃ to form a phosphite composition comprising four primary reaction products.

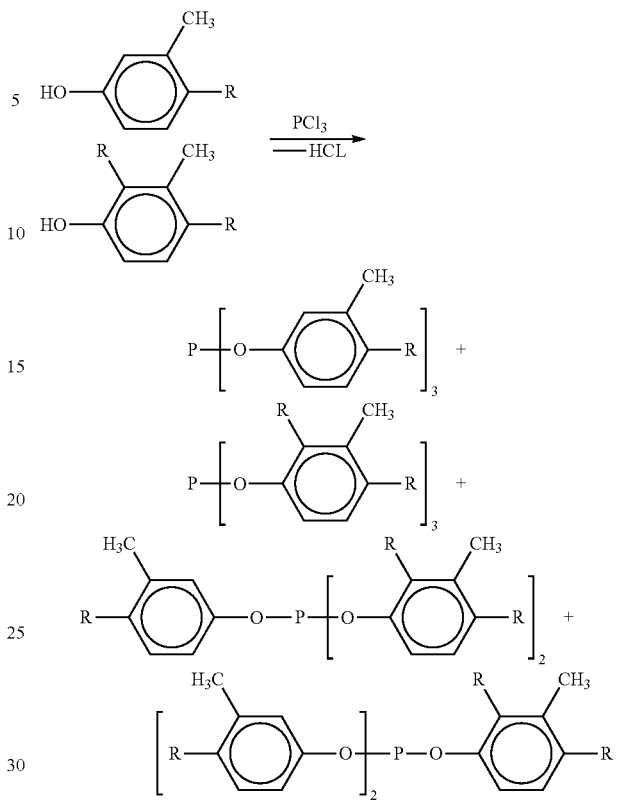

Wherein R is $R_4$, $R_5$, and $R_6$ as defined above, except not hydrogen. Note that a minor amount of other alkylated cresols, e.g., ortho/ortho disubstituted-m-cresols, may be included as additional reactants in the above reaction scheme and would form additional derivative phosphites, but these additional reactants and products have been omitted from this reaction for clarity.

Stabilizers

As discussed above, a stabilizing amount or effective amount of the phosphite composition derived from cresols of the invention may be used as a secondary antioxidant for various types of polymers. As used herein, by "stabilizing amount" and an "effective amount" it is meant when the polymer composition containing the phosphites of the invention shows improved stability in any of its physical or color properties in comparison to an analogous polymer composition which does not include a phosphite composition of the invention. Examples of improved stability include improved stabilization against, for example, molecular weight degradation, color degradation, and the like from, for example, melt processing, weathering, and/or long term field exposure to air heat, light, and/or other elements. In one example, improved stability is obtained in the form of one or both of lower initial color as measured by yellowing index and melt flow rate of the molten polymer or additional resistance to weathering, as measured, for example, by initial yellowness index (YI), or by resistance to yellowing and change in color, when compared to a composition without the stabilizer additive.

The additives and stabilizers described herein are preferably present in an amount effective to improve composition stability. When one of the aforementioned phosphite compositions is utilized, the mixture is generally present in an amount from about 0.001 to about 5 wt. %, e.g., from about 0.0025 to about 2 wt. % or from about 0.005 to about 1 wt. %, based on the total weight of the polymer including the weight of the phosphite composition and any other stabilizers or additives. The phosphite compositions of this invention stabilize polymers especially during high temperature processing with relatively little change in melt index and/or color, even after multiple extrusions.

The invention further relates to a stabilized thermoplastic resins, comprising a base polymer and any of the aforementioned phosphite compositions of the invention. The base polymer may be a polyolefin, and the liquid phosphite composition may be used with a co stabilizer, for example, hindered phenolics, aromatic amines, hydroxylamines, alkylamine-N-oxides, lactones, and thioethers. Thus, the thermoplastic resins stabilized by the phosphite composition of the present invention may optionally contain one or more additional stabilizers or mixtures of stabilizers selected from the group consisting of the phenolic antioxidants, hindered amine light stabilizers (HALS), the ultraviolet light absorbers, phosphites, phosphonites, alkaline metal salts of fatty acids, hydrotalcites, metal oxides, epoxidized soybean oils, the hydroxylamines, the tertiary amine oxides, lactones, thermal reaction products of tertiary amine oxides, and the thiosynergists.

In one embodiment, the amount of each component in the stabilizing composition, based on the total weight percent of the polymer or polymeric resin, is shown in Table 2.

TABLE 2

| Component | Range | Preferred Range |
|---|---|---|
| Liquid phosphite compositions | 0.001-5.0 wt % | 0.005-1.0 wt % |
| Primary antioxidant | 0-5.0 wt % | 0.005-2.0 wt % |
| UV or light stabilizers | 0-3.0 wt % | 0.001-2.0 wt % |
| Metal deactivators | 0-3.0 wt % | 0.001-2.0 wt % |
| Other secondary antioxidants | 0-3.0 wt % | 0.001-2.0 wt % |
| Peroxide scavengers | 0-3.0 wt % | 0.001-2.0 wt % |
| Polyamide stabilizers | 0-3.0 wt % | 0.001-2.0 wt % |
| Basic co-stabilizers | 0-3.0 wt % | 0.001-2.0 wt % |
| Nucleating and clarifying agents | 0-3.0 wt % | 0.001-2.0 wt % |
| Aminoxy propanoate | 0-3.0 wt % | 0.001-2.0 wt % |

The phosphite composition of the invention or the resulting stabilized polymer compositions optionally also comprise primary antioxidants such as the following:

(i) Alkylated monophenols, for example: 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2,6-bis(α-methylbenzyl)-4-methylphenol, 2-(α-methylcyclohexyl)-4,6-dimethylphenol, 2,6-dioctadecyl-4-methylphenol, 2,4,6-tricyclohexyphenol, and 2,6-di-tert-butyl-4-methoxymethylphenol. Commercially available alkylated monophenols include Lowinox™ 624 and Naugard™ 431 made by Chemtura Corp. Other phenols are commercially available such as BHEB.

(ii) Alkylated hydroquinones, for example, 2,6-di-tert-butyl-4-methoxyphenol, 2,5-di-tert-butyl-hydroquinone, 2,5-di-tert-amyl-hydroquinone, and 2,6-diphenyl-4-octadecyloxyphenol. Commercially available alkylated hydroquinones include Lowinox AH25 made by Chemtura.

(iii) Hydroxylated thiodiphenyl ethers, for example, 2,2'-thio-bis-(6-tert-butyl-4-methylphenol), 2,2'-thio-bis-(4-octylphenol), 4,4'-thio-bis-(6-tert-butyl-3-methylphenol), and 4,4'-thio-bis-(6-tert-butyl-2-methylphenol). Commercially available hydroxylated thiodiphenyl ethers include Lowinox TMB6, and Lowinox TBP6 made by Chemtura.

(iv) Alkylidene-bisphenols, for example, 2,2'-methylene-bis-(6-tert-butyl-4-methylphenol), 2,2'-methylene-bis-(6-tert-butyl-4-ethylphenol), 2,2'-methylene-bis-(4-methyl-6-(α-methylcyclohexyl)phenol), 2,2'-methylene-bis-(4-methyl-6-cyclohexylphenol), 2,2'-methylene-bis-(6-nonyl-4-methylphenol), 2,2'-methylene-bis-(6-nonyl-4-methylphenol), 2,2'-methylene-bis-(6-(α-methylbenzyl)-4-nonylphenol), 2,2'-methylene-bis-(6-(alpha,alpha-dimethylbenzyl)-4-nonyl-phenol), 2,2'-methylene-bis-(4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenol)butane, 1,1-bis(2-methyl-4-hydroxy-5-tert-butylphenyl)butane, 2,2'-isobutylidene-bis(4,6-dimethylphenol), 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-dodecyl-mercaptobutane, ethyleneglycol-bis-(3,3-bis-(3'-tert-butyl-4'-hydroxyphenyl)-butyrate)-di-(3-tert-butyl-4-hydroxy-5-methylphenyl)-dicyclopentadiene, and di-(2-(3'-tert-butyl-2' hydroxy-5' methyl-benzyl)-6-tert-butyl-4-methylphenyl)terephthalate. Commercially available alkylidene-bisphenols include Lowinox 22M46, Lowinox WSP, Lowinox 44B25, Naugard 536, Naugawhite™, and Lowinox 221B46 made by Chemtura.

(v) Benzyl compounds, for example, 1,3,5-tris-(3,5-di-tert-butyl-4-hydroxybenzyl)-2,4,6-trimethylbenzene, bis-(3,5-di-tert-butyl-4-hydroxybenzyl)sulfide, isooctyl 3,5-di-tert-butyl-4-hydroxybenzyl-mercapto-acetate, bis-(4-tert-butyl-3-hydroxy-2,6-dimethylbenzyl)dithiol-terephthalate, 1,3,5-tris-(3,5-di-tert-butyl-4 hydroxybenzyl)isocyanurate, 1,3,5-tris-(4-tert-butyl-3-hydroxy-2,6-dimethylbenzyl) isocyanurate, 1,3,5-tris(4-t-butyl-3-hydroxy-2,6-dimethylbenzyl)-1,3,5-Triazine-2,4,6-(1H,3H,5H)-trione, dioctadecyl-3,5-di-tert-butyl-4-hydroxybenzyl-phosphonate, calcium salt of monoethyl 3,5-di-tert-butyl-4-hydroxybenzylphosphonate, 1,3,5-tris-(3,5-dicyclohexyl-4-hydroxybenzyl)isocyanurate. Commercially available benzyl compounds include Anox™ IC-14, Anox 330 and Lowinox 1790 made by Chemtura.

(vi) Acylaminophenols, for example, 4-hydroxylauric acid anilide, 4-hydroxy-stearic acid amilide, 2,4-bis-octylmercapto-6-(3,5-tert-butyl-4-hydroxyanilino)-s-triazine, and octyl-N-(3,5-di-tert-butyl-4-hydroxyphenyl)-carbamate.

(vii) Esters of beta-(3,5-di-tert-butyl-4-hydroxyphenol)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethylisocyanurate, thiodiethyleneglycol, di-hydroxyethyl oxalic acid diamide. Such phenols also include tetrakis[methylene {3,5-di-tert-butyl-4-hydroxycinnamate}] methane. Commercially available esters include Anox 20, Anox 1315, Lowinox GP45, Naugalube 38, Naugalube 531, Anox PP18, Naugard PS48 and Naugard XL-1 made by Chemtura.

(viii) Thio esters of beta-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, dihydroxyethyl oxalic acid diamide. Commercially available thio esters include Naugalube™ 15 and Anox 70 made by Chemtura.

(ix) Amides of beta-(3,5-di-tert-butyl-4-hydroxyphenol)-propionic acid for example, N,N'-di-(3,5-di-tert-butyl-4-hydroxyphenylpropionyl)-hexammethylen-diamine, N,N'-di-(3,5-di-tert-butyl-4-hydroxyphenylpropionyl)

trimethylenediamine, N,N'-di-(3,5-di-tert-butyl-4-hydroxyphenylpropionyl)-hydrazine, N,N'-Hexamethylene bis[3-(3,5-di-t-butyl-4-hydroxyphenyl)propionamide, and 1,2-Bis(3,5-di-tert-butyl-4-hydroxyhydrocinnamoyl)hydrazine. Commercially available amides include Lowinox HD98 and Lowinox MD24 made by Chemtura.

(x) Other phenolic antioxidants include the following phenols: Polymeric phenols such as the reaction product of 4-methylphenol with dicyclopentadiene and isobutylene, commercially available as Lowinox CPL; Chemtura. Alkylidene-poly-phenols, such as 1,3 tris(3-methyl-4-hydroxyl-5-t-butyl-phenyl)-butane (Lowinox CA22; Chemtura). Thio phenols such as 2,6-di-tert-butyl-4-(4,6-bis(octylthio)-1,3,5-triazin-2-ylamino)phenol (Irganox™ 565; Ciba), 4,6-bis(octylthiomethyl)-o-cresol (Irganox 1520; Ciba); 4,6-bis(dodecylthiomethyl)-o-cresol (Irganox 1726; Ciba). Hydroxylamines, such as bis(octadecyl)hydroxylamine (Irgastab™ FS 042; Ciba). Ester phenols include bis[3,3-bis(4-hydroxy-3-tert-butyl phenyl)butanoic acid]glycol ester (Hostanox™ O3; Clariant Chemicals). Still other phenols include 2-[1-2-hydroxy-3,5-di-tert-pentylphenyl)ethyl]-4,6-di-tert-pentylphenyl acrylate (Sumilizer™ GS; Sumitomo Chemical).

In one embodiment, the stabilizing composition comprises one phenolic selected from the group consisting of tetrakis-methylene (3,5-di-t-butyl-4-hydroxylhydrocinnamate) methane (Anox 20), 1,3,5-tris(3,5-di-t-butyl-4-hydroxybenzyl)isocyanurate (Anox IC-14), 1,3,5-tris(4-tert.-butyl-3-hydroxy-2,6-dimethylbenzyl)-1,3,5-triazine-2,4,6-(1H,3H,5H)-trione (Lowinox 1790), octyl-3-(3,5-di-t-butyl-4-hydroxyphenyl)propionate (Anox PP18), bis(octadecyl)hydroxylamine (Irgastab FS-042), 1,3,5-trimethyl-2,4,6-tris (3,5-di-tert-4-hydroxybenzyl)benzene (Anox 330), 2,6-bis (α-methylbenzyl)-4-methylphenol (Naugalube 431), 3,5-bis (1,1-dimethylethyl)-4-hydroxy-benzenepropanoic acid (Anox 1315), 2,6-di-t-butyl-4-ethyl-phenol (BHEB), and mixtures thereof, and the liquid phosphite composition defined herein.

The phosphite compositions and/or the resulting stabilized polymeric resin compositions optionally also comprise one or more UV absorbers and/or light stabilizers, such as the following:

(i) 2-(2'-hydroxyphenyl)-benzotriazoles, for example, the 5'-methyl-, 3'5'-di-tert-butyl-, 3'5'-di-tert-amyl-, 5'-tert-butyl-, 5'-tert-amyl-, 5'(1,1,3,3-tetramethylbutyl)-, 5-chloro-3', 5'-di-tert-butyl-, 5-chloro-3'-tert-butyl-5'-methyl-, 3'-sec-butyl-5'-tert-butyl-,4'-octoxy, 3',5'-ditert-amyl-3',5'-bis-(α,α-dimethylbenzyl)-derivatives. Commercially available 2-(2'-hydroxyphenyl)-benzotriazoles include Lowilite™ 26, Lowilite 27, Lowilite 28, Lowilite 29, Lowilite 35, Lowilite 55, and Lowilite 234 made by Chemtura.

(ii) 2-Hydroxy-benzophenones, for example, the 4-hydroxy, 4-methoxy-, 4-octoxy, 4-decyloxy-, 4-dodecyloxy-, 4-benzyloxy-, 2,4-dihydroxy-, 4,2',4'-trihydroxy- and 2'-hydroxy-4,4'-dimethoxy-derivative. Exemplary 2-hydroxy-benzophenones include 2-hydroxy-4-methoxybenzophenone, 2-hydroxy-4-ethoxybenzophenone, 2,4-dihydroxybenzophenone, and 2-hydroxy-4-propoxybenzophenone. Commercially available 2-(2'-hydroxyphenyl)-benzotriazoles include Lowilite 20, Lowilite 22, Lowilite 20S, and Lowilite 24 made by Chemtura.

(iii) Esters of substituted and unsubstituted benzoic acids for example, phenyl salicylate, 4-tert-butylphenyl-salicilate, octylphenyl salicylate, dibenzoylresorcinol, bis-(4-tert-butylbenzoyl)-resorcinol, benzoylresorcinol, 2,4-di-tert-butyl-phenyl-3,5-tert-butyl-4-hydroxybenzoate and hexadecyl-3,5-di-tert-butyl-4-hydroxybenzoate.

(iv) UV absorbers and light stabilizers may also comprise acrylates, for example, alpha-cyano-beta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyano-vinyl)-2-methyl-indoline.

(v) Nickel compounds are also suitable UV absorbers and light stabilizers. Exemplary nickel compounds include nickel complexes of 2,2'-thio-bis(4-(1,1,1,3-tetramethylbutyl)-phenol), such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-penyl undecyl ketoxime, nickel complexes of 1-phenyl-4-lauroyl-5-hydroxy-pyrazole, optionally with additional ligands. Commercially available nickel compounds include Lowilite Q84 (2,2'-Thiobis(4-tert-octyl-phenolato))-N-butylamine-Nichel(II) made by Chemtura.

(vi) Sterically hindered amines may be used as UV absorbers and light stabilizers. Sterically hindered amines, for example bis(2,2,6,6-tetramethylpiperidyl)-sebacate, bis-(1, 2,2,6,6-pentamethylpiperidyl)-sebacate, n-butyl-3,5-di-tert-butyl-4-hydroxybenzyl malonic acid bis(1,2,2,6,6-pentamethylpiperidyl)ester, condensation product of 1-hydroxyethyl-2,2,6,6-tetramethyl-4-hydroxy-piperidine and succinic acid, condensation product of N,N'-(2,2,6,6-tetramethylpiperidyl)-hexamethylendiamine and 4-tert-octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetra-carbonic acid, 1,1'(1,2-ethanediyl)-bis-(3,3,5,5-tetramethylpiperazinone). Such amines include hydroxylamines derived from hindered amines, such as di(1-hydroxy-2,2,6,6-tetramethylpiperidin-4-yl)sebacate: 1-hydroxy 2,2,6,6-tetramethyl-4-benzoxypiperidine; 1-hydroxy-2,2,6,6-tetramethyl-4-(3,5-di-tert-butyl-4-hydroxy hydrocinnamoyloxy)-piperidine; and N-(1-hydroxy-2,2,6,6-tetramethyl-piperidin-4-yl)-epsiloncaprolactam. Commercially available hindered amines include Lowilite 19, Lowilite 62, Lowilite 77, Lowilite 92 and Lowilite 94 made by Chemtura.

(vii) Oxalic acid diamides, for examples, 4,4'-dioctyloxy-oxanilide, 2,2'-di-octyloxy-5',5'-di-tert-butyloxanilide, 2,2'-di-dodecyloxy-5',5' di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2' ethyl-5,4-di-tert-butyloxanilide and mixtures of o- and p-methoxy—as well as of o- and p-ethoxy-disubstituted oxanilides.

Polymer(s) stabilized with phosphite composition of the invention may also include one or more additional additives, including, for example, one or more of the following:

(i) Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydrophenylpropionyl)-hydrazine, salicyloylamino-1,2,4-triazole, bis-benzyliden-oxalic acid dihydrazide.

(ii) Additional secondary antioxidants such as additional phosphites and/or phosphonites, for example, triphenyl phosphite, diphenylalkyl phosphites, phenyldialkyl phosphites, tris(nonyl-phenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite tristearyl sorbitol triphosphite, bis(2,4-dicumylphenyl)pentaerythritol diphosphite, and tetrakis(2,4-di-tert-butylphenyl)-4,4'-biphenylene diphosphonite. Commercially available secondary antioxidants include Naugalube TPP, Alkanox™ 240, Ultranox™ 626, Naugard P, Weston™ 399, Weston TNPP, Weston 430, Weston 618F, Weston 619F, Weston DPDP, Weston DPP, Weston PDDP, Weston PTP, Weston TDP, Weston TLP, Weston TPP, and Weston TLTTP (trilauryl trithio phosphite) made by Chemtura; Doverphos™ 4, Doverphos 4-HR, Doverphos 4-HR Plus, Doverphos HiPure 4, and Doverphos S-9228 made by Dover Chemical; and Hostanox PEPQ made by Clariant Chemicals.

(iii) Peroxide scavengers, for example, esters of betathiodipropionic acid, for example the lauryl, stearyl, myristyl or tridecyl esters, mercaptobenzimidazole or the zinc salt of 2-mercaptobenzimidazole, zinc-dibutyldithiocaramate, dioctadecyldisulfide, pentaerythritoltetrakis-(beta-dodecylmercapto)-propionate.

(iv) Polyamide stabilizers, for example copper salts in combination with iodides and/or phosphorus compounds and salts of divalent manganese may also be included in the polymer and/or phosphite composition.

(v) Basic co-stabilizers, for example, melamine, polyvinylpyrrolidone, dicyandiamide, triallyl cyanurate, urea derivatives, hydrazine derivatives, amines, polyamides, polyurethanes, hydrotalcites, alkali metal salts and alkaline earth metal salts of higher fatty acids, for example, Ca stearate, calcium stearoyl lactate, calcium lactate, Zn stearate, Zn octoate, Mg stearate, Na ricinoleate and K palmirate, antimony pyrocatecholate or zinc pyrocatecholate. Commercially available co-stabilizers include Mark™ 6045, Mark 6045ACM, Mark 6055, Mark 6055ACM, Mark 6087ACM, Mark 6102, Mark CE 345, Mark CE 350, and Mark CE 387, made by Chemtura; and DHT-4A™ made by Kisuma Chemicals.

(vi) Nucleating and clarifying agents, for example, metal salts of 4-tert butylbenzoic acid, adipic acid, diphenylacetic acid, sorbitol and derivatives thereof, sodium benzoate, and benzoic acid.

(vii) Aminoxy propanoate derivatives such as methyl-3-(N,N-dibenzylaminoxy)propanoate; ethyl-3-(N,N-dibenzylaminoxy)propanonoate; 1,6-hexamethylene-bis(3-N,N-dibenzylaminoxy)proponoate); methyl-(2-(methyl)-3(N,N-dibenzylaminoxy)propanoate); octadecyl-3-(N,N-dibenzylaminoxy)propanoic acid; tetrakis(N,N-dibenzylaminoxy)ethyl carbonyl oxymethy)methane; octadecyl-3-(N,N-diethylaminoxy)-propanoate; 3-(N,N-dibenzylaminoxy)propanoic acid potassium salt; and 1,6-hexamethylene bis(3-(N-allyl-N-dodecyl aminoxy)propanoate).

(viii) Other additives, for example, plasticizers, lubricants, emulsifiers, pigments, optical brighteners, flameproofing agents, anti-static agents, blowing agents and thiosynergists such as dilaurylthiodipropionate or distearylthiodipropionate.

Optionally in the polymer or polymeric resins there may also be from 5-50 wt %, e.g., 10-40 wt % or 15-30 wt % of fillers and reinforcing agents, for example, calcium carbonate, silicates, glass fibers, asbestos, talc, kaolin, mica, barium sulfate, metal oxides and hydroxides, carbon black and graphite.

Polymers

The invention further pertains to a stabilized polymer, wherein one component comprises a liquid phosphite composition of the present invention and the other a polymer, such as a polyolefin, polyvinyl chloride, etc., or polymeric resins.

The polymer stabilized by such liquid phosphite compositions may be any polymer known in the art, such as polyolefin homopolymers and copolymers, thermoplastics, rubbers, polyesters, polyurethanes, polyalkylene terephthalates, polysulfones, polyimides, polyphenylene ethers, styrenic polymers and copolymers, polycarbonates, acrylic polymers, polyamides, polyacetals, halide-containing polymers, biodegradable polymers, and mixtures thereof. Mixtures of different polymers, such as polyphenylene ether/styrenic resin blends, polyvinyl chloride/ABS or other impact modified polymers, such as methacrylonitrile and α-methylstyrene containing ABS, and polyester/ABS or polycarbonate/ABS and polyester plus some other impact modifier may also be used. Such polymers are available commercially or may be made by means well known in the art. However, the stabilizer compositions of the invention are particularly useful in thermoplastic polymers, such as polyolefins, polycarbonates, polyesters, polyphenylene ethers and styrenic polymers, due to the extreme temperatures at which thermoplastic polymers are often processed and/or used.

The polymers used in combination with liquid phosphite composition of the present invention are produced using a variety of polymerization processes including solution, high-pressure, slurry and gas phase using various catalysts including Ziegler-Natta, single-site, metallocene or Phillips-type catalysts. Non-limiting polymers useful with the liquid phosphite compositions include ethylene based polymers such as linear low density polyethylene, elastomers, plastomers, high density polyethylene, substantially linear long chain branched polymers, and low density polyethylene; and propylene based polymers such as polypropylene polymers including atactic, isotactic, and syndiotactic polypropylene polymers, and propylene copolymers such as propylene random, block or impact copolymers.

The polymers, typically ethylene based polymers, have a density in the range of from 0.86 g/cc to 0.97 g/cc, preferably in the range of from 0.88 g/cc to 0.965 g/cc, more preferably in the range of from 0.900 g/cc to 0.96 g/cc, even more preferably in the range of from 0.905 g/cc to 0.95 g/cc, yet even more preferably in the range from 0.910 g/cc to 0.940 g/cc, and most preferably greater than 0.915 g/cc, preferably greater than 0.920 g/cc, and most preferably greater than 0.925 g/cc. The polymers produced by the process of the invention typically have a molecular weight distribution, a weight average molecular weight to number average molecular weight (Mw/Mn) of greater than 1.5 to about 15, particularly greater than 2 to about 10, more preferably greater than about 2.2 to less than about 8, even more preferably from about 2.2 to less than 5, and most preferably from 2.5 to 4. The ratio of Mw/Mn can be measured by gel permeation chromatography techniques well known in the art. The polymers of the present invention in one embodiment have a melt index (MI) or (I2) as measured by ASTM-D-1238-E in the range from 0.01 dg/min to 1000 dg/min, more preferably from about 0.01 dg/min to about 100 dg/min, even more preferably from about 0.1 dg/min to about 50 dg/min, and most preferably from about 0.1 dg/min to about 10 dg/min. The polymers of the invention in one embodiment have a melt index ratio (I21/I2) (I21 is measured by ASTM-D-1238-F) of from 10 to less than 25, more preferably from about 15 to less than 25. The polymers of the invention in a preferred embodiment have a melt index ratio (I21/I2) (I21 is measured by ASTM-D-1238-F) of from preferably greater than 25, more preferably greater than 30, even more preferably greater that 40, still even more preferably greater than 50 and most preferably greater than 65.

Polymers used with liquid phosphites compositions of the invention are useful in such forming operations as film, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, geomembranes, and pond liners. Molded articles include single and multi-layered constructions in the form of bottles, tanks, large hollow articles, rigid food containers and toys, etc. In addition to the above, the liquid phosphite compositions are used in various rubber based products such as tires, barriers and the like.

In one embodiment, the liquid phosphite composition is approved for use in polymers, preferably polyolefins, that are used in contact with beverages, foods and other human consumables.

Polymers of monoolefins and diolefins, for example polypropylene, polyisobutylene, polybutene-1, polymethylpentene-1, polyisoprene, or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example, mixtures of polypropylene with polyisobutylene, polypropylene with polyethylene (for example PP/HDPE, PP/LDPE) and mixtures of different types of polyethylene (for example LDPE/HDPE), may also be used. Also useful are copolymers of monoolefins and diolefins with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene, isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidene-norbornene; as well as mixtures of such copolymers and their mixtures with polymers mentioned above, for example polypropylene/ethylene propylene-copolymers, LDPE/EVA, LDPE/EAA, LLDPE/EVA, and LLDPE/EAA.

The olefin polymers may be produced by, for example, polymerization of olefins in the presence of Ziegler-Natta catalysts optionally on supports such as, for example, $MgCl_2$, chromium 20 salts and complexes thereof, silica, silica-alumina and the like. The olefin polymers may also be produced utilizing chromium catalysts or single site catalysts, e.g., metallocene catalysts such as, for example, cyclopentadiene complexes of metals such as Ti and Zr. As one skilled in the art would readily appreciate, the polyethylene polymers used herein, e.g., LLDPE, can contain various comonomers such as, for example, 1-butene, 1-hexene and 1-octene comonomers.

Polymers may also include styrenic polymers, such as polystyrene, poly-(p-methylstyrene), 5 poly-(α-methylstyrene), copolymers of styrene or α-methylstyrene with dienes or acrylic derivatives, such as, for example, styrene/butadiene (SBR), styrene/acrylonitrile, styrene/alkyl methacrylate, styrene/maleic anhydride, styrene/maleimide, styrene/butadiene/ethyl acrylate, styrene/acrylonitrile/methylacrylate, mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene (SBS), styrene/isoprene/styrene (SIS), styrene/ethylene/butylene/styrene or styrene/ethylene/propylene/styrene.

Styrenic polymers may additionally or alternatively include graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene and copolymers thereof; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene-propylene-diene terpolymers, styrene and acrylonitrile on polyacrylates or polymethacrylates, styrene and acrylonitrile on acrylate/butadiene copolymers, as well as mixtures thereof with the styrenic copolymers indicated above.

Suitable rubbers include both natural rubber and synthetic rubbers, and combinations thereof. Synthetic rubbers include, but are not limited to, for example, thermoplastic rubbers, ethylene/alpha-olefin/non-conjugated polyene (EPDM) rubbers, ethylene/alpha-olefin (EPR) rubbers, styrene/butadiene rubbers, acrylic rubbers, nitrile rubbers, polyisoprene, polybutadiene, polychloroprene, acrylonitrile/butadiene (NBR) rubbers, polychloroprene rubbers, polybutadiene rubbers, isobutylene-isoprene copolymers, etc. Thermoplastic rubbers include SIS, solution and emulsion SBS, etc.

Nitrile polymers are also useful in the polymer composition of the invention. These include homopolymers and copolymers of acrylonitrile and its analogs, such as polymethacrylonitrile, polyacrylonitrile, acrylonitrile/butadiene polymers, acrylonitrile/alkyl acrylate polymers, acrylonitrile/alkyl methacrylate/butadiene polymers, and various ABS compositions as referred to above in regard to styrenics.

Polymers based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be stabilized with the phosphite compositions of the present invention. These include polymers such as polychloroprene, epichlorohydrin homo- and copolymers, polyvinyl chloride, polyvinyl bromide, polyvinyl fluoride, polyvinylidene chloride, chlorinated polyethylene, chlorinated polypropylene, fluorinated polyvinylidene, brominated polyethylene, chlorinated rubber, vinyl chloride-vinyl acetate copolymers, vinyl chloride-ethylene copolymer, vinyl chloride-propylene copolymer, vinyl chloridestyrene copolymer, vinyl chloride-isobutylene copolymer, vinyl chloride-vinylidene chloride copolymer, vinyl chloride-styrene-maleic anhydride terpolymer, vinyl chloride-styrene-acrylonitrile copolymer, vinyl chloride-butadiene copolymer, vinyl chloride isoprene copolymer, vinyl chloride-chlorinated propylene copolymer, vinyl chloride-vinylidene chloride-vinyl acetate terpolymer, vinyl chloride-acrylic acid ester copolymers, vinyl chloride-maleic acid ester copolymers, vinyl chloride-methacrylic acid ester copolymers, vinyl chloride-acrylonitrile copolymer and internally plasticized polyvinyl chloride.

Other useful polymers include homopolymers and copolymers of cyclic ethers, such as polyalkylene glycols, polyethylene oxide, polypropylene oxide or copolymers thereof with bisglycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acids and diols and/or from hydroxycarboxylic acids or the corresponding lactones, such as polyethylene terephthalate, polybutylene terephthalate, poly-1,4dimethylol-cyclohexane terephthalate, poly-2-(2,2,4(4-hydroxyphenyl)-propane) terephthalate and polyhydroxybenzoates as well as block copolyetheresters derived from polyethers having hydroxyl end groups.

Polyamides and copolyamides which are derived from bisamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylene bisamine and adipic acid; polyamides prepared from hexamethylene bisamine and isophthalic or/and terephthalic acid and optionally an elastomer as modifier, for example poly-2,4,4 trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols and polyamides or copolyamides modified with EPDM or ABS may be used.

In another embodiment, the polymer comprises a biodegradable polymer or compostable polymer. Biodegradable polymers are those in which the degradation results from the action of naturally occurring microorganisms, such as bacteria, fungi and algae. Compostable polymers undergoes degradation by biological processes during composting to yield $CO_2$, water, inorganic compounds and a biomass at a rate consistent with other compostable materials. Typically the biodegradable or compostable polymers are derived from plant sources and are synthetically produced. Examples of biodegradable or compostable polymers include poly(glycolic acid) (PGA), poly(lactic acid) (PLA), and co-polymers thereof. Biodegradable or compostable polymers may also be derived from a blend of starch of a plant and a conventional petroleum-based polymer. For example, the biodegradable polymer may be blended with a polyolefin.

Polyolefin, polyalkylene terephthalate, polyphenylene ether and styrenic polymers, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred.

In one embodiment, the liquid phosphite compositions are added to stabilize natural and synthetic waxes, such as n-paraffin waxes, chloroparaffins, α-olefin waxes, microcrystalline waxes, polyethylene waxes, amide waxes, and Fisher-Tropsch waxes. These waxes may be suitable for making candles.

The instant stabilizers may readily be incorporated into the polymer by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized compositions of the invention may optionally also contain from about 0.001 to about 5 wt. %, e.g., from about 0.0025 to about 2 wt. % or from about 0.05 to about 0.25 wt. %, of various conventional additives, such as those described previously, or mixtures thereof.

The stabilizers of this invention advantageously assist with the stabilization of polymer compositions especially in high temperature processing against changes in melt index and/or color, even though the polymer may undergo a number of extrusions. The stabilizers of the present invention may readily be incorporated into the polymer compositions by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer.

The compositions of the present invention can be prepared by a variety of methods, such as those involving intimate admixing of the ingredients with any additional materials desired in the formulation. Suitable procedures include solution blending and melt blending. Because of the availability of melt blending equipment in commercial polymer processing facilities, melt processing procedures are generally preferred. Examples of equipment used in such melt compounding methods include: co-rotating and counter-rotating extruders, single screw extruders, disc-pack processors and various other types of extrusion equipment. In some instances, the compounded material exits the extruder through small exit holes in a die and the resulting strands of molten resin are cooled by passing the strands through a water bath. The cooled strands can be chopped into small pellets for packaging and further handling.

All of the ingredients may be added initially to the processing system, or else certain additives may be pre-compounded with each other or with a portion of the polymer or polymeric resin to make a stabilizer concentrate. Moreover, it is also sometimes advantageous to employ at least one vent port to allow venting (either atmospheric or vacuum) of the melt. Those of ordinary skill in the art will be able to adjust blending times and temperatures, as well as component addition location and sequence, without undue additional experimentation.

While the stabilizers of this invention may be conveniently incorporated by conventional techniques into polymers before the fabrication thereof into shaped articles, it is also possible to apply the instant stabilizers by a topical application to the finished articles. Articles may comprise the instant stabilizer compounds and polymers and may be made into, for example, head lamp covers, roofing sheets, telephone covers, aircraft interiors, building interiors, computer and business machine housings, automotive parts, and home appliances. The articles may be made by extrusion, injection molding, roto-molding, compaction, and other methods. This may be particularly useful with fiber applications where the instant stabilizers are applied topically to the fibers, for example, by way of a spin finish during the melt spinning process.

The phosphite composition of the invention may have uses in addition to polymer stabilization. For example, it may be desirable to react the phosphite composition to form a new derivative product, that may of additional uses. Transesterification processes, for example, such as those disclosed in Hechenbleikner et al., U.S. Pat. No. 3,056,823, which is incorporated herein by reference, may also be employed. Specifically, the process described by Hechenbleikner et al. involves transesterifying a triaryl phosphite with a monohydroxy hydrocarbon in the presence of a small but catalytically effective amount of a metal alcoholate or metal phenolate. To avoid contamination, the alcoholate of the particular alcohol to be transesterified is employed. Instead of employing a preformed alcoholate, the alcoholate can be formed in situ by adding the metal, e.g., sodium, potassium or lithium to the alcohol prior to adding the triaryl phosphite. The mono alcohol and triaryl phosphite are reacted in the mol ratio of three mols of the alcohol to one mol of the triaryl phosphite.

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner.

The present invention will now be described by way of the following non-limiting examples.

Example 1

2-tert-butyl-4-methylphenol (144.4 g, 0.96 mols) and 4-tert-butylphenol (157.9 g, 0.96 mols) are charged to a jacketed vessel. The reagents are heated to 70° C. under nitrogen and agitated when molten. When the internal temperature is stable at 70° C., the phosphorus trichloride (80.2 g, 0.58 mols) is added. Phosphorus trichloride is added at a uniform rate, below the surface of the cresylic and phenolic mixture, over 3 hours. During the addition the temperature is ramped from 70° C. to 150° C. The resultant HCl off-gas is absorbed by a scrubbing unit. Once all the phosphorus trichloride had been added, temperature of the reaction mixture is held at 150° C. for 1 hour, or until HCl evolution has ceased. Next the reaction mass is heated from 150° C. to 200° C. over 1 hour. Once the reaction has reached 200° C., the reaction is degassed by applying a water vacuum (60-80 mbar of pressure) until the total chlorine content is less than 50 ppm. The excess butylated cresylics and phenolics are removed by distillation under a pressure of 9 mbar up to an internal temperature of 198° C. The reaction yielded 291.7 g of phosphite. The resulting mixture of phosphites had a kinematic viscosity of 4145 cSt at 40° C. and 308 cSt at 60° C. The phosphorous content is 6.1%.

Example 2

Phosphorus trichloride (80.2 g, 0.58 mols) and N,N-dimethyldodecylamine (1.74 ml, 6.41 mmols) are charged to a jacketed vessel under nitrogen. The reagents are stirred and heated to 70° C. A powdered blend of 2-tert-butyl-4-methylphenol (164.25 g, 0.906 mols) and 4-tert-amylphenol (164.25 g, 0.906 mols) is prepared and added in shots of equal weight every 15 minutes to the phosphorus trichloride and N,N-dimethyldodecylamine. The reaction temperature is held at 70° C. during the addition. After the addition has been completed the temperature is ramped from 70° C. to 150° C. over 1 hr, and the reaction mixture is held at 150° C. for 1 hour, or until HCl evolution has ceased. Next the reaction mass is heated from 150° C. to 200° C. over 1 hour. Once the reaction has reached 200° C., the reaction is degassed by applying a water vacuum (60-80 mbar of pressure) until the total chlorine content is less than 50 ppm. The excess cresylics and phenolics are removed by distillation under a pressure of 8 mbar up to an internal temperature of 198° C. The reaction yielded 245 g of phosphite. The resulting mixture of phosphites had a kinematic viscosity of 3247 cSt at 40° C. and 352 cSt at 60° C. The phosphorous content is 5.9%.

Example 3

Para-cresol (75 g, 0.69 mols), meta-cresol (75 g, 0.69 mols) and trifluoromethanesulphonic acid (18 µL, 0.2 mmols) are charged to an oil jacketed flask. The reagents are heated to 70° C. under nitrogen and agitated when the cresols are molten. When the internal temperature is steady 70° C. the addition of isobutene (136.5 g, 2.43 mols) is started. The isobutene is added at a uniform rate via a sintered glass frit below the surface of the cresols over 5 hours. After the addition is completed, the reaction mass is held at a jacket temperature of 70° C. for one hour and then sodium carbonate (0.2 g, 1.9 mmols) is added. The alkylate is purified by vacuum distillation, the un-alkylated cresols is removed in a fraction that distils under a pressure of 50 mbar up to an internal temperature of 130° C. (cresols content<1%). The main fraction distills under a pressure of 2-3 mbar up to an internal temperature of 132° C. (vapor temperature 124° C.), yielding 217 g of mixed butylated cresols.

The butylated cresylic alkylate comprised the following components: 27.3 wt. % 2-t-butyl-m-cresol; 39 wt. % 2-t-butyl-p-cresol; 23.6 wt. % 2,6-di-t-butyl-p-cresol; and 8.8 wt. % isomers of di-butyl-m-cresol.

Example 4

Molten butylated cresylic alkylate prepared in Example 3 (198.4 g, 1.11 mols) is charged to a jacketed vessel and heat to 70° C. under nitrogen. When the internal temperature is stable at 70° C., the addition of phosphorus trichloride (44.4 g, 0.32 mols) is started. Phosphorus trichloride is added at a uniform rate, below the surface of the cresylic mixture, over 3 hours. During the addition the temperature is ramped from 70° C. to 150° C. The resultant HCl off-gas is absorbed by a scrubbing unit. Once all the phosphorus trichloride had been added, the reaction mixture is held at 150° C. for 1 hour, or until HCl evolution has ceased. Next the reaction mass is heated from 150° C. to 200° C. over 1 hour. Once the reaction has reached 200° C., the reaction is degassed by applying a water vacuum (60-80 mbar of pressure) until the total chlorine content is less than 50 ppm. The excess butylated cresylics is removed by distillation under a pressure of 7 mbar up to an internal temperature of 200° C. The reaction yielded 157.3 of phosphite.

Example 5

Multipass Extrusion

This example illustrates the stabilizing effectiveness of the liquid phosphite compositions of the present invention upon multipass extrusion in linear low density polyethylene (LLDPE).

The base formulation contained 500 ppm of zinc stearate and 200 ppm of Anox™ PP18 [octadecyl-3-(3',5'-di-tert-butyl-4-hydroxyphenyl)propionate]. A liquid phosphite composition of the present invention (with 0.75 wt. % triisopropanolamine) are also added to the base polymer, such that 17 ppm of phosphorous are present in the polymer. Weston™ 399 is used as a standard in this study. The stabilized resin formulation are extruded from a 19 mm diameter Brabender single-screw extruder at 60 rpm, with the four heating zones being set to the following temperatures: 200° C.; 225° C.; 250° C. and 270° C.

The extrudate was cooled by passing it through an ice water bath and then pelletised. These pellets were re-extruded. After the first, third and fifth extrusion passes the melt flow rate (in g/10 min) was measured at 230° C./2.16 kg and 230° C./21.6 kg. A relatively small increase in melt flow index means insignificant polymer degradation, or good stabilization. After the first, third and fifth extrusion passes the yellowing index was recorded. The results are shown in Table 3.

TABLE 3

|  | Example 1 | Example 2 | Example 4 | Weston 399 |
|---|---|---|---|---|
| Composition | | | | |
| LLDPE | 99.902 wt % | 99.901 wt % | 99.8985 wt % | 99.89 wt % |
| ZnSt | 0.05 wt % | 0.05 wt % | 0.05 wt % | 0.05 wt % |
| Anox PP18 | 0.02 wt % | 0.02 wt % | 0.02 wt % | 0.02 wt % |
| Phosphite Amount | 0.028 wt % | 0.029 wt % | 0.0315 wt % | 0.04 wt % |
| YI (ASTM E313) during multipass @ 230° C. | | | | |
| Initial | −1.228 | −1.07 | −0.883 | −1.249 |
| Pass 1 | 0.512 | 0.573 | 0.548 | 0.06 |
| Pass 3 | 1.027 | 0.952 | 1.013 | 0.718 |
| Pass 5 | 2.712 | 1.689 | 1.455 | 1.203 |
| MFI @2.16 kg during multipass @ 230° C. | | | | |
| Initial | 0.960 | 0.958 | 0.955 | 0.967 |
| Pass 1 | 0.928 | 0.909 | 0.911 | 0.904 |
| Pass 3 | 0.744 | 0.781 | 0.730 | 0.778 |
| Pass 5 | 0.659 | 0.629 | 0.625 | 0.637 |
| MFI @21.6 kg during multipass @ 230° C. | | | | |
| Initial | 22.921 | 22.817 | 22.900 | 23.027 |
| Pass 1 | 23.100 | 22.986 | 22.667 | 23.066 |
| Pass 3 | 22.346 | 21.656 | 21.783 | 21.614 |
| Pass 5 | 20.851 | 20.694 | 20.596 | 20.973 |
| MFI ratio during multipass @ 230° C. | | | | |
| Initial | 23.875 | 23.814 | 23.971 | 23.819 |
| Pass 1 | 24.884 | 25.298 | 24.880 | 25.519 |
| Pass 3 | 30.016 | 27.741 | 29.843 | 27.765 |
| Pass 5 | 31.663 | 32.894 | 32.965 | 32.940 |
| YI, after NOx exposure | | | | |
| 2 hours | 2.90 | 2.84 | 2.95 | 3.26 |
| 25 hours | 6.29 | 8.33 | 8.99 | 6.27 |
| 94 hours | 9.81 | 9.14 | 10.03 | 9.34 |

TABLE 3-continued

|  | Example 1 | Example 2 | Example 4 | Weston 399 |
|---|---|---|---|---|
| 120 hours | 10.53 | 9.94 | 10.90 | 10.11 |
| 140 hours | 11.54 | — | — | 10.52 |

At equivalent phosphorous loading (17 ppm) the phosphites of the invention (i.e., Examples 1, 2 and 4) demonstrate (within experimental error) equivalent performance to Weston™ 399. However, this equivalent performance is achieved using a significantly lower weight percentage loading of the phosphites of the invention, e.g., 0.029 wt % of Example 2 affords the equivalent protection as 0.04 wt % loading of Weston™ 399.

Example 6

Stabilizer Compositions for PP

Melt Flow Index

This example illustrates the stabilizing effectiveness of the liquid phosphite composition of the present invention upon multipass extrusion in poly(propylene).

The base polymer was a Basell HF500N Spheripol homopolymer poly(propylene) powder with a melt-flow index (MFI) of 12 grams/10 minutes. The base formulation also contained 500 ppm of calcium stearate as an acid scavenger. All formulations were made up by adding 500 ppm each of Anox™ 20 (tetrakis[methylene {3,5-di-tert-butyl-4-hydroxycinnamate}]methane) and a corresponding liquid phosphite composition of the present invention to the base polymer. The stabilized resin formulation are extruded from a 19 mm diameter Brabender single-screw extruder at 60 rpm, with the four heating zones being set to the following temperatures: 200° C.; 225° C.; 250° C. and 270° C. under oxygen.

The extrudate was cooled by passing it through an ice water bath and then pelletized. These pellets were re-extruded. After the third extrusion pass the melt flow rate (in g/10 min) was measured at 230° C./2.16 kg. A relatively small increase in melt flow index means insignificant polymer degradation, or good stabilization. The closer the melt flow rate is after the fifth extrusion relative to the melt flow rate after the first extrusion, the more effective is the process stabilization achieved. The results are shown in Table 4.

TABLE 4

| | Primary | | Secondary | | Melt Flow Index (g/10 min) | | |
|---|---|---|---|---|---|---|---|
| | | Amount | | Amount | | | |
| Run | Type | (ppm) | Type | (ppm) | Pass 1 | Pass 3 | Pass 5 |
| Unstabilized | — | — | — | — | 21.9 | 32.0 | 46.3 |
| Comparative* | Anox 20 | 500 | Alkanox 240 | 500 | 13.7 | 15.3 | 17.1 |
| 1 | Anox 20 | 500 | Example 1 | 500 | 12.5 | 13.8 | 15.4 |
| 2 | Anox 20 | 500 | Example 1 | 1000 | 12.1 | 12.6 | 13.3 |

*Anox BB011: 1/1 blend of Anox 20 and Alkanox 240

At a 500 ppm loadlevel the phosphite composition of Example 1 demonstrated increase performance against Alkanox 240, and a superior result versus the unstabilized PP. Note that the performance increase by doubling the load in run 2 was not significant, which may indicate a saturation/solubility issue of the stabilizer in PP.

Each of the liquid secondary antioxidants showed superior melt stabilization versus the base. The results from this study show that the phosphite derived from cresol in Example 2 had a slightly improved melt stabilization compared with phosphites derived from phenols.

Example 7

Stabilizer Compositions for PP

Yellowness Index

Using the same PP compositions as Example 6, the phosphite composition of Example 1 is measured for yellowness index (YI) using ASTM E 313. Low YI values indicate less yellowing. The lower the YI value, the more effectively does the stabilizer system prevent yellowing and damage of the organic polymeric material.

TABLE 5

| Run | Primary Type | Amount (ppm) | Secondary Type | Amount (ppm) | Yellow Index Pass 1 | Pass 3 | Pass 5 |
|---|---|---|---|---|---|---|---|
| Unstabilized | — | — | — | — | −1.548 | 0.367 | 2.284 |
| Comparative* | Anox 20 | 500 | Alkanox 240 | 500 | 0.87 | 7.851 | 12.544 |
| 1 | Anox 20 | 500 | Example 1 | 500 | 0.155 | 8.433 | 14.390 |
| 2 | Anox 20 | 500 | Example 1 | 1000 | −1.369 | 1.969 | 5.766 |

*Anox BB011: 1/1 blend of Anox 20 and Alkanox 240

As shown in Table 5, when the load level of phosphite composition of Example 1 is increased to 1000 ppm, the yellow index improves versus the comparative. Based on this, the stabilizers with 1000 ppm of phosphite compositions more effectively prevent the discoloration of the polymer due to the phenolic antioxidant.

In view of the many changes and modifications that can be made without departing from principles underlying the invention, reference should be made to the appended claims for an understanding of the scope of the protection to be afforded the invention.

What is claimed is:

1. A composition comprising a liquid phosphite, said liquid phosphite consisting of a mixture of at least two different phosphites of structure (I)

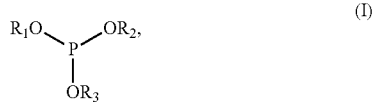

(I)

wherein $R_1$, $R_2$, and $R_3$ are independently selected alkylated aryl groups selected from the group consisting of t-butylphenyl, di-t-butylphenyl, t-amylphenyl, di-t-amylphenyl and cresyl of structure (III),

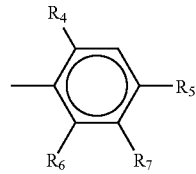

(III)

wherein $R_4$, $R_5$, and $R_6$ are independently selected from the group consisting of hydrogen, methyl, t-butyl and t-amyl; and $R_7$ is hydrogen or methyl;

wherein one of $R_4$, $R_5$, $R_6$, and $R_7$ is methyl and at least one of $R_4$, $R_5$, and $R_6$, is t-butyl or t-amyl provided that at least one of the phosphites comprises an alkylated cresyl of structure (III), wherein the liquid phosphite consisting of a mixture of at least two different phosphites of structure (I) is a liquid at ambient conditions.

2. The composition of claim 1, wherein the phosphite comprising an alkylated cresyl group is selected from the group consisting of tris(4-t-butyl-m-cresyl)phosphite, tris(2-t-butyl-m-cresyl)phosphite, tris(4,6-di-t-butyl-m-cresyl)phosphite, bis(4-t-butyl-m-cresyl)-4,6-di-t-butyl-m-cresyl phosphite, bis(2-t-butyl-m-cresyl)-4-t-butyl-m-cresyl phosphite, bis(2-t-butyl-m-cresyl)-4,6-di-t-butyl-m-cresyl phosphite, bis(4,6-di-t-butyl-m-cresyl)-4-t-butyl-m-cresyl phosphite, bis(4,6-di-t-butyl-m-cresyl)-2-t-butyl-m-cresyl phosphite, tris(4-t-amyl-m-cresyl)phosphite, tris(2-t-amyl-m-cresyl) phosphite, tris(4,6-di-t-amyl-m-cresyl)phosphite, bis(4-t-amyl-m-cresyl)-2-t-amyl-m-cresyl phosphite, bis(4-t-amyl-m-cresyl)-4,6-di-t-amyl-m-cresyl phosphite, bis(2-t-amyl-m-cresyl)-4-t-amyl-m-cresyl phosphite, bis(2-t-amyl-m-cresyl)-4,6-di-t-amyl-m-cresyl phosphite, bis(4,6-di-t-amyl-m-cresyl)-4-t-amyl-m-cresyl phosphite, and bis(4,6-di-t-amyl-m-cresyl)-2-t-amyl-m-cresyl phosphite.

3. The composition of claim 1, wherein the phosphite comprises an alkylated cresyl group is selected from the group consisting of tris(2-t-butyl-p-cresyl)phosphite, tris(2,6-di-t-butyl-p-cresyl)phosphite, bis(2-t-butyl-p-cresyl)-2,6-di-t-butyl-p-cresyl phosphite, bis(2,6-di-t-butyl-p-cresyl)-2-t-butyl-p-cresyl phosphite, tris(2-t-amyl-p-cresyl)phosphite, tris (2,6-di-t-amyl-p-cresyl)phosphite, bis(2-t-amyl-p-cresyl)-2,6-di-t-amyl-p-cresyl phosphite, and bis(2,6-di-t-amyl-p-cresyl)-2-t-amyl-p-cresyl phosphite.

4. The composition of claim 1, wherein the liquid phosphite is derived from a mixture of 5-95 wt % alkylated m-cresol and 5-95 wt % alkylated p-cresol.

5. The composition of claim 1, wherein at least two different phosphites are derived from a mixture of 5-95 wt % of an alkylated cresol and 5-95 wt % of an alkylated phenol.

6. The composition of claim 1, wherein the liquid phosphite comprises the following:
   tris(monoalkylaryl)phosphite in an amount from 20 to 70 wt %;
   bis(monoalkylaryl)dialkylaryl phosphite in an amount from 15 to 60 wt %,
   tris(dialkylaryl)phosphite in an amount of from 0.1 to 20 wt %; or
   bis(dialkylaryl)monoalkylaryl phosphite in an amount of from 2 to 20 wt %
wherein monoalkylaryl is selected from the group consisting of t-butylphenyl, t-amylphenol, and cresyl of structure (III) wherein one of $R_4$, $R_5$, and $R_6$ is t-butyl or t-amyl; and dialkylaryl is selected from the group consisting of di-t-butylphenyl, di-t-amylphenyl and cresyl of structure (III) wherein two of $R_4$, $R_5$, and $R_6$ are t-butyl or t-amyl.

7. A composition according to claim 1 comprising:
   a polymer; and
   the liquid phosiphite.

8. The composition of claim 7, wherein the polymer is selected from the group consisting of polyolefin homopolymers and copolymers, thermoplastics, rubbers, polyesters, polyurethanes, polyalkylene terephthalates, polysulfones, polyimides, polyphenylene ethers, styrenic polymers and copolymers, polycarbonates, acrylic polymers, polyamides, polyacetals, halide-containing polymers, biodegradable polymers, and mixtures thereof.

9. The composition of claim 7, further comprising a primary phenolic antioxidant.

10. The composition of claim 9, wherein the primary phenolic antioxidants are selected from the group consisting of tetrakismethylene (3,5-di-t-butyl-4-hydroxylhydrocinnamate)methane, 1,3,5-tris(3,5-di-t-butyl-4-hydroxybenzyl)isocyanurate, 1,3,5-tris(4-t-butyl-3-hydroxy-2,6-dimethylbenzyl)-1,3,5-triazine-2,4,6-(1H,3H,5H)-trione, octyl-3-(3,5-di-t-butyl-4-hydroxyphenyl)propionate, bis(octadecyl)hydroxylamine, 1,3,5-trimethyl-2,4,6-tris(3,5-di-t-4-hydroxybenzyl)benzene, 2,6-bis(α-methylbenzyl)-4-methylphenol, 3,5-bis(1,1-dimethylethyl)-4-hydroxybenzenepropanoic acid, and 2,6-di-t-butyl-4-ethyl-phenol and mixtures thereof.

* * * * *